(12) United States Patent
Yang et al.

(10) Patent No.: US 8,309,747 B2
(45) Date of Patent: Nov. 13, 2012

(54) PROCESS FOR SYNTHESIZING BRIDGED CYCLOPENTADIENYL-INDENYL METALLOCENES

(75) Inventors: Qing Yang, Bartlesville, OK (US); Mark L. Hlavinka, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 232 days.

(21) Appl. No.: 12/830,591

(22) Filed: Jul. 6, 2010

(65) Prior Publication Data

US 2012/0010421 A1    Jan. 12, 2012

(51) Int. Cl.
   *C07F 15/00* (2006.01)
(52) U.S. Cl. ............... 556/12; 556/11; 556/28; 556/53
(58) Field of Classification Search .......... 556/11, 556/12, 28, 53
   See application file for complete search history.

(56) References Cited

U.S. PATENT DOCUMENTS

| | | | |
|---|---|---|---|
| 7,026,494 | B1 | 4/2006 | Yang et al. |
| 7,064,225 | B2 | 6/2006 | Thorn et al. |
| 7,420,097 | B2 | 9/2008 | Thorn et al. |
| 7,468,452 | B1 | 12/2008 | Martin et al. |
| 7,572,948 | B2 | 8/2009 | Martin et al. |
| 2008/0242812 | A1 | 10/2008 | Ruchatz et al. |
| 2008/0312380 | A1 | 12/2008 | Kwalk |
| 2009/0163569 | A1* | 6/2009 | Tobler et al. .......... 514/406 |

OTHER PUBLICATIONS

International Search Report, PCT/US2011/042928, dated Sep. 16, 2011.

Alt, Helmut G., et al., Verbruckte Indenyliden-Cyclopentaclienylidenkomplexde des Typs ($C_9H_5CH_2Ph$-X-$C_5H_4$) $MCI_2$ (X=$CMe_2$. $SiMe_2$; M=Zr, Hf) als Metallocenkatalysatoren fur die Ethylenpolyrnersation. Die Molekulstrukturen von ($C_9H_5CH_2Ph$-$CMe_2C_5H_4$)$_{MCl2}$ (M=Zr, Hf), J of Organo Chem 558 (1998) 111-121.

Fierro, R., at al. Asymmetric Zirconocene Precursors for Catalysis of Propylene Polymerization, J of Polymer Science: Part A: Polymer Checmistry, vol. 32, 2817-2824 (1994.

Gomez, FJ, et al. Syndiospecific Porpylene Polymerization Using $C_1$-Symmetric ansa-Metallocene Catalysts: Sustituent and Bridge Effects, Macromolecules 2002, 35, 3358-3368.

U.S. Appl. No. 12/466,229, entitled "Method and System for Forming a Precursor Compound for Non-Bridged Unsymmetric Polyolefin Polymerization Catalyst," (IFW accessible), filed May 14, 2009.

Stone et al., "An Exceptionally Simple and Efficient Method for the Preparation of a Wide Variety of Fulvenes," The Journal of Organic Chemistry, 1984, vol. 49, No. 11, pp. 1849-1853.

* cited by examiner

*Primary Examiner* — Porfirio Nazario Gonzalez
(74) *Attorney, Agent, or Firm* — Merchant & Gould P.C.

(57) ABSTRACT

The present invention provides methods of making bridged cyclopentadienyl-indenyl metallocene compounds. Generally, these methods can be conducted without the use of a fine purification process such as distillation, chromatography, and crystallization.

20 Claims, 3 Drawing Sheets

PROCESS FOR SYNTHESIZING BRIDGED CYCLOPENTADIENYL-INDENYL METALLOCENES

BACKGROUND OF THE INVENTION

The present invention relates generally to the synthesis of metallocene compounds. These metallocene compounds may be used as components in a multi-component catalyst system, ultimately for use in olefin polymerizations or other catalytic processes. More specifically, this invention relates to methods of synthesizing certain bridged cyclopentadienyl-indenyl metallocene compounds.

Many multi-step synthesis procedures for metallocene compounds involve fine purification processes to separate and/or purify intermediate components at each step in the synthesis procedure. These fine purification processes—including distillation, chromatography, crystallization, and the like—can add time, cost, and complexity to the metallocene synthesis.

It would be beneficial to develop new synthetic methods to produce bridged cyclopentadienyl-indenyl metallocene compounds in acceptable yields without the use of expensive, complex, and time-consuming fine purification steps. Accordingly, it is to this end that the present invention is directed.

SUMMARY OF THE INVENTION

The present invention discloses methods for synthesizing bridged cyclopentadienyl-indenyl metallocene compounds. These compounds can be used in catalysts systems for the polymerization of olefins.

Methods of making metallocene compounds having the formula:

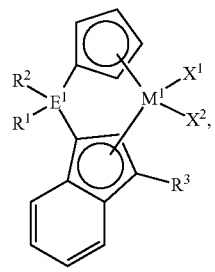

(I)

are disclosed. In accordance with an aspect of this invention, a method of making a metallocene compound having formula (I) uses a fulvene and a substituted indenyl as the starting materials. This method comprises:

(i) contacting a compound having the formula:

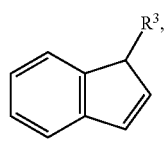

(IVa)

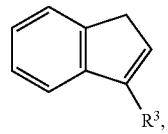

(IVb)

or a combination thereof,
with a first strong base in the presence of a first solvent to form a first mixture;

(ii) contacting the first mixture with a compound having the formula:

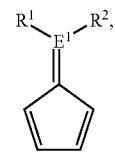

(III)

in the presence of a second solvent to form a crude ligand product comprising a compound having the formula:

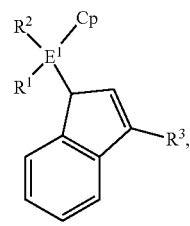

(Va)

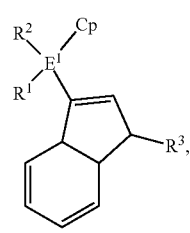

(Vb)

or a combination thereof;

(iii) contacting the crude ligand product comprising the compound having formula (Va), (Vb), or a combination thereof, with a second strong base in the presence of a third solvent to form an intermediate mixture comprising a dianion of the compound having formula (Va), (Vb), or a combination thereof; and (iv) contacting the intermediate mixture comprising the dianion of the compound having formula (Va), (Vb), or a combination thereof, with $M^1X^1X^2L^1L^2$ in the presence of a fourth solvent and an optional hydrocarbon co-solvent to form a reaction mixture comprising the metallocene compound having formula (I);

wherein:
$M^1$ is Ti, Zr, or Hf;
$X^1$ and $X^2$ are independently F; Cl; Br; I; $SO_3CF_3$; or $SO_3R$, wherein R is an alkyl, aryl, or alkylaryl group having up to 18 carbon atoms;
$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C, Si, Ge, or Sn;

$R^1$ and $R^2$ are independently H, a hydrocarbyl group having up to 18 carbon atoms, or $R^1$ and $R^2$ are connected to a form a cyclic or heterocyclic group having up to 18 carbon atoms; and $R^3$ is a hydrocarbyl or hydrocarbylsilyl group having up to 18 carbon atoms.

In other aspects of this invention, methods of making a metallocene compound having formula (I) using different starting materials are disclosed. For instance, bridged cyclopentadienyl-indenyl metallocenes can be synthesized from cyclopentadiene and a substituted indenyl, from a fulvene and indene, or from cyclopentadiene and indene.

Generally, the synthesis methods disclosed herein provide acceptable yield and purity of the desired metallocene compound, and the use of the crude metallocene compound in a catalyst system produces polymers with acceptable properties. Yet, the synthesis methods do not require a fine purification step, such as distillation, chromatography, crystallization, and the like.

DEFINITIONS

Figure 1:
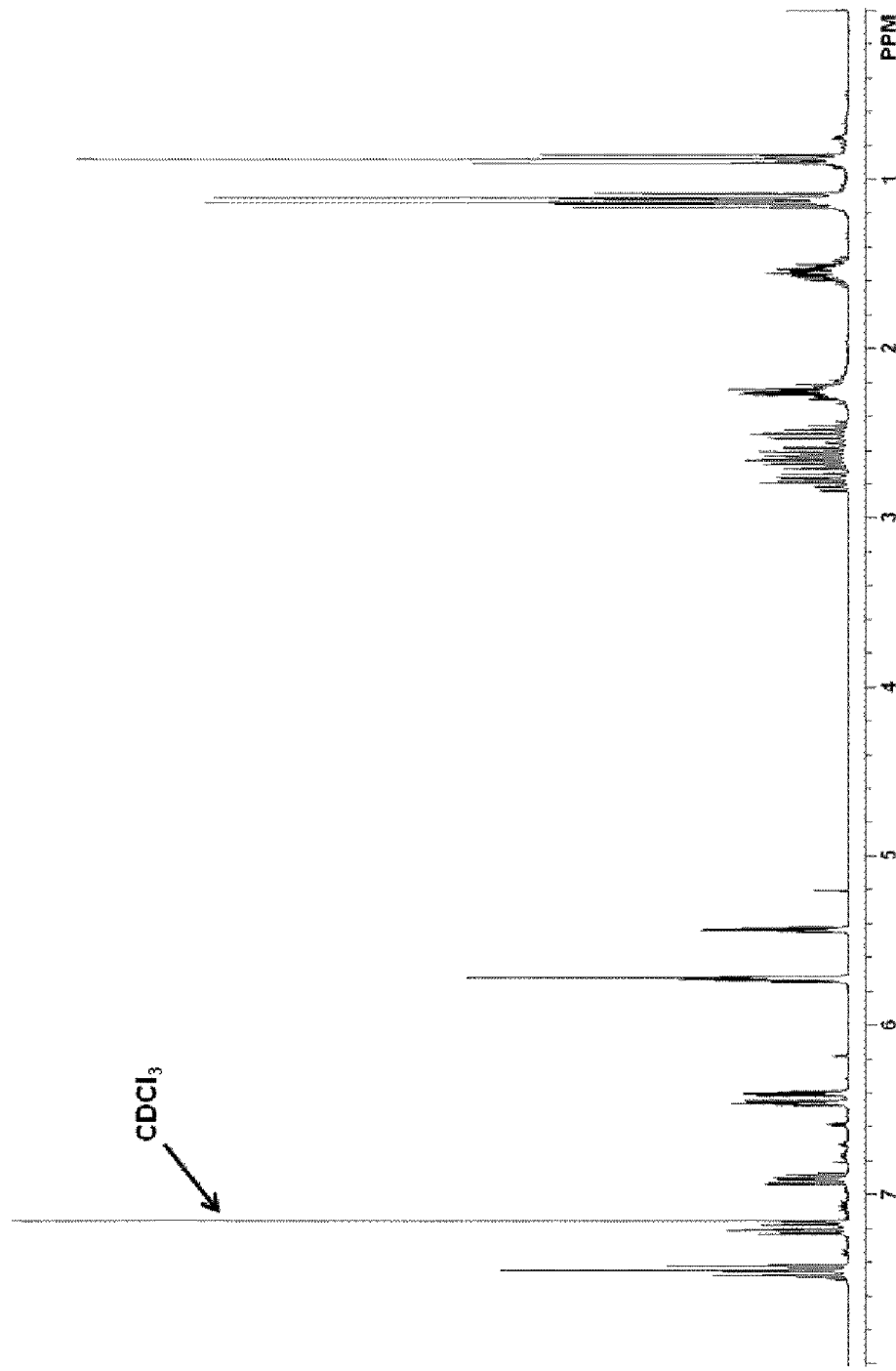
FIG. 1 presents a $^1$H-NMR plot of the final product of Example 1 containing MET I.

To define more clearly the terms used herein, the following definitions are provided. To the extent that any definition or usage provided by any document incorporated herein by reference conflicts with the definition or usage provided herein, the definition or usage provided herein controls.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "contact product" is used herein to describe compositions wherein the components are contacted together in any order, in any manner, and for any length of time. For example, the components can be contacted by blending or mixing. Further, contacting of any component can occur in the presence or absence of any other component. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which may be blended, mixed, slurried, dissolved, reacted, treated, or otherwise contacted in some other manner. Therefore, the term "contacting" encompasses the "reacting" of two or more components, and it also encompasses the "mixing" or "blending" of two or more components that do not react with one another.

The term "in the presence of" a particular solvent is used herein to indicate that the components that are contacted or reacted in steps of a synthesis can occur "in" the solvent (e.g., in solution), but this is not a requirement. For instance, one or more of the components can be dissolved in the solvent. Additionally or alternatively, one or more of the components can be partially or completely insoluble in the solvent. Thus, the use of "in the presence of" a particular solvent is meant to include both single phase and multi-phase reaction systems. In many cases, one component can be dissolved in a solvent when contacted or reacted with one or more other components.

The term "metallocene," as used herein, describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

For any particular compound disclosed herein, any general or specific structure presented also encompasses all conformational isomers, regioisomers, and stereoisomers that may arise from a particular set of substituents, unless stated otherwise. Also, unless stated otherwise, the general or specific structure also encompasses all enantiomers, diastereomers, and other optical isomers whether in enantiomeric or racemic forms, as well as mixtures of stereoisomers, as would be recognized by a skilled artisan.

Applicants disclose several types of ranges in the present invention. These include, but are not limited to, a range of number of atoms, a range of molar ratios, a range of temperatures, a range of times, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ alkyl group, or in alternative language an alkyl group having up to 18 carbon atoms, as used herein, refers to a moiety that can be selected independently from an alkyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ alkyl group), and also including any combination of ranges between these two numbers (for example, a $C_2$ to $C_4$ and a $C_{12}$ to $C_{16}$ alkyl group).

Similarly, another representative example follows for the molar ratio of cyclopentadiene to the compound having formula (II) provided in one aspect of this invention. By a disclosure that the molar ratio of cyclopentadiene to the compound having formula (II) can be in a range from about 2:1 to about 1:1, Applicants intend to recite that the molar ratio can be about 2:1, about 1.95:1, about 1.9:1, about 1.85:1, about 1.8:1, about 1.75:1, about 1.7:1, about 1.65:1, about 1.6:1, about 1.55:1, about 1.5:1, about 1.45:1, about 1.4:1, about 1.35:1, about 1.3:1, about 1.25:1, about 1.2:1, about 1.15:1, about 1.1:1, about 1.05:1, or about 1:1. Additionally, the molar ratio can be within any range from about 2:1 to about 1:1 (for example, from about 1.5:1 to about 1.1:1), and this also includes any combination of ranges between about 2:1 and about 1:1 (for example, the molar ratio is in a range from about 1.95:1 to about 1.75:1, or from about 1.35:1 to about 1.051). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The terms "a," "an," and "the" are intended to include plural alternatives, e.g., at least one, unless otherwise specified. For instance, the disclosure of "a solvent" or "a base" is meant to encompass one, or mixtures or combinations of more than one, solvent or base, respectively.

While compositions and methods are described in terms of "comprising" various components or steps, the compositions and methods can also "consist essentially of" or "consist of" the various components or steps. For example, a method of making a metallocene compound of the present invention can comprise; alternatively, can consist essentially of; or alternatively, can consist of; step (i), step (ii), step (iii), and step (iv).

The following abbreviations are used in this disclosure:

Bu—n-butyl (also n-Bu)
Cp—cyclopentadienyl
Et—ethyl
Ind—indenyl
Me—methyl
Ph—phenyl
Pr—n-propyl
t-Bu—tert-butyl or t-butyl

DETAILED DESCRIPTION OF THE INVENTION

The present invention is directed generally to processes for synthesizing bridged cyclopentadienyl-indenyl metallocene compounds.

Synthesis of a Bridged Cyclopentadienyl-Indenyl Metallocene from a Fulvene and a Substituted Indenyl In accordance with the present invention, methods of making metallocene compounds having the formula:

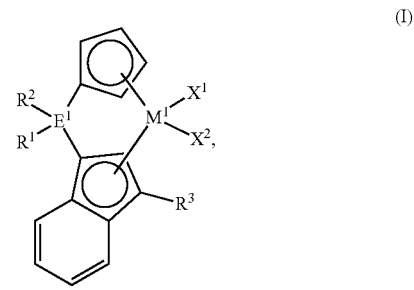

(I)

are disclosed.

Such compounds can be used in catalyst compositions, for example, in the polymerization of olefins to form homopolymers, copolymers, terpolymers, and the like.

In accordance with an aspect of this invention, a method of making a metallocene compound having formula (I) is provided and, in this aspect, the method comprises:

(i) contacting a compound having the formula:

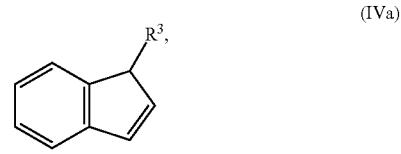

(IVa)

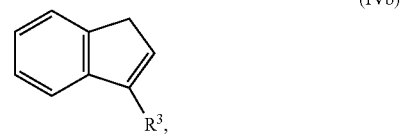

(IVb)

or a combination thereof, with a first strong base in the presence of a first solvent to form a first mixture;

(ii) contacting the first mixture with a compound having the formula:

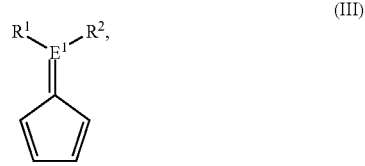

(III)

in the presence of a second solvent to form a crude ligand product comprising a compound having the formula:

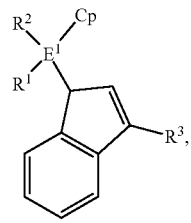
(Va)

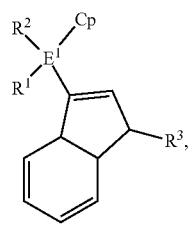
(Vb)

or a combination thereof;

(iii) contacting the crude ligand product comprising the compound having formula (Va), (Vb), or a combination thereof, with a second strong base in the presence of a third solvent to form an intermediate mixture comprising a dianion of the compound having formula (Va), (Vb), or a combination thereof; and (iv) contacting the intermediate mixture comprising the dianion of the compound having formula (Va), (Vb), or a combination thereof, with $M^1X^1X^2L^1L^2$ in the presence of a fourth solvent and an optional hydrocarbon co-solvent to form a reaction mixture comprising the metallocene compound having formula (I).

In the method of making a metallocene compound having formula (I), $M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C, Si, Ge, or Sn;

$R^1$ and $R^2$ are independently H, a hydrocarbyl group having up to 18 carbon atoms, or $R^1$ and $R^2$ are connected to a form a cyclic or heterocyclic group having up to 18 carbon atoms; and $R^3$ is a hydrocarbyl or hydrocarbylsilyl group having up to 18 carbon atoms.

Unless otherwise specified, formulas (I), (III), (IVa), (IVb), (Va), and (Vb) above, any other structural formulas disclosed herein, and any species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

As one of skill in the art would recognize, the compound having formula (IVa) and the compound having formula (IVb) are isomers (likewise, for the compound having formula (Va) and the compound having formula (Vb)). The methods of this invention may utilize a starting material which is a single isomer (e.g., a compound having formula (IVa)), or which is a mixture or combination of isomers. Likewise, methods of this invention may produce intermediate or final products that are a single isomer (e.g., a compound having formula (Va)) or that are a mixture or combination of isomers.

Hydrocarbyl is used herein to specify a hydrocarbon radical group that includes, but is not limited to, aryl, alkyl, alkylaryl, cycloalkyl, alkenyl, cycloalkenyl, cycloalkadienyl, alkynyl, aralkyl, aralkenyl, aralkynyl, and the like, and includes all substituted, unsubstituted, linear, and/or branched derivatives thereof. Unless otherwise specified, the hydrocarbyl groups of this invention typically comprise up to about 18 carbon atoms. In another aspect, hydrocarbyl groups can have up to 12 carbon atoms, for instance, up to 10 carbon atoms, up to 8 carbon atoms, or up to 6 carbon atoms. A hydrocarbyloxide group, therefore, is used generically to include both alkoxide and aryloxide groups, and these groups can comprise up to about 18 carbon atoms. Illustrative and non-limiting examples of alkoxide and aryloxide groups (i.e., hydrocarbyloxide groups) include methoxy, ethoxy, propoxy, butoxy, phenoxy, substituted phenoxy, and the like. The term hydrocarbylamino group is used generically to refer collectively to alkylamino, arylamino, dialkylamino, diarylamino groups, and the like. Unless otherwise specified, the hydrocarbylamino groups of this invention comprise up to about 18 carbon atoms. Hydrocarbylsilyl groups include, but are not limited to, alkylsilyl groups, alkenylsilyl groups, arylsilyl groups, arylalkylsilyl groups, and the like, which have up to about 18 carbon atoms. For example, illustrative hydrocarbylsilyl groups can include trimethylsilyl and phenyloctylsilyl. These hydrocarbyloxide, hydrocarbylamino, and hydrocarbylsilyl groups can have up to 12 carbon atoms; alternatively, up to 10 carbon atoms; or alternatively, up to 8 carbon atoms, in other aspects of the present invention.

Unless otherwise specified, alkyl groups and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, decyl, and the like. Illustrative examples of alkenyl groups within the scope of the present invention include, but are not limited to, ethenyl, propenyl, butenyl, pentenyl, hexenyl, heptenyl, octenyl, nonenyl, decenyl, and the like. The alkenyl group can be a terminal alkenyl group, but this is not a requirement. For instance, specific alkenyl group substituents can include, but are not limited to, 3-butenyl, 4-pentenyl, 5-hexenyl, 6-heptenyl, 7-octenyl, 3-methyl-3-butenyl, 4-methyl-3-pentenyl, 1,1-dimethyl-3-butenyl, 1,1-dimethyl-4-pentenyl, and the like.

In this disclosure, an aryl group encompasses aryl and arylalkyl groups including, but not limited to, phenyl, alkyl-substituted phenyl (e.g., tolyl, xylyl), naphthyl, alkyl-substituted naphthyl, and the like. In this disclosure, an alkylaryl group encompasses phenyl-substituted alkyl, naphthyl-substituted alkyl, and the like, and such moieties can include, but are not limited to, benzyl (—$CH_2Ph$), phenylethyl (—$CH_2CH_2Ph$), phenylpropyl, phenylbutyl, 2-propyl-phenylethyl, and the like. Unless otherwise specified, any aryl or alkylaryl moiety used herein is meant to include all regioisomers; for example, the term tolyl is meant to include any possible substituent position, that is, ortho, meta, or para.

In the method of making a metallocene compound having formula (I), $M^1$ is Ti, Zr, or Hf. In some aspects disclosed herein, $M^1$ is Zr or Hf; alternatively, $M^1$ is Zr; or alternatively, $M^1$ is Hf.

$X^1$ and $X^2$ are independently F; Cl; Br; I; $SO_3CF_3$; or $SO_3R$, wherein R is an alkyl, aryl, or alkylaryl group having up to 18 carbon atoms or, alternatively, up to 12 carbon atoms. For instance, R can be methyl, ethyl, propyl, butyl, pentyl, hexyl, heptyl, octyl, nonyl, or decyl, and the like.

$X^1$ and $X^2$ independently can be F, Cl, Br, or I in one aspect of this invention. In another aspect, both $X^1$ and $X^2$ can be Cl; alternatively, both $X^1$ and $X^2$ can be F; alternatively, both $X^1$ and $X^2$ can be Br; or alternatively, both $X^1$ and $X^2$ can be I.

$L^1$ and $L^2$ independently can be F; Cl; Br; I; methyl; benzyl; phenyl; H; $BH_4$; $SO_3CF_3$; $OBR_2$ or $SO_3R$, wherein R is an alkyl, aryl, or alkylaryl group; or a hydrocarbyloxide group, a hydrocarbylamino group, or a hydrocarbylsilyl group. The hydrocarbyloxide group, the hydrocarbylamino group, the hydrocarbylsilyl group and R can have up to 18 carbon atoms or, alternatively, up to 12 carbon atoms.

$L^1$ and $L^2$ independently can be F, Cl, Br, I, benzyl, phenyl, or methyl. For example, $L^1$ and $L^2$ independently are Cl, benzyl, phenyl, or methyl in one aspect of this invention. In another aspect, $L^1$ and $L^2$ independently are benzyl, phenyl, or methyl. Yet, in another aspect, both $L^1$ and $L^2$ can be Cl; alternatively, both $L^1$ and $L^2$ can be benzyl; alternatively, both $L^1$ and $L^2$ can be phenyl; or alternatively, both $L^1$ and $L^2$ can be methyl.

Cp in formulas (Va) and (Vb) is a cyclopentadienyl group. As shown in these formulas, the cyclopentadienyl group is unsubstituted, i.e., other than $E^1$. In the method of making a metallocene compound having formula (I), $E^1$ is C, Si, Ge, or Sn. In one aspect of this invention, $E^1$ is C. In another aspect, $E^1$ is Si. In yet another aspect, $E^1$ is Ge. In still another aspect, $E^1$ is Sn.

$R^1$ and $R^2$ are independently H; a hydrocarbyl group having up to 18 carbon atoms or, alternatively, up to 12 carbon atoms; or $R^1$ and $R^2$ are connected to a form a cyclic or heterocyclic group having up to 18 carbon atoms or, alternatively, up to 12 carbon atoms. Cyclic groups include cycloalkyl and cycloalkenyl moieties and such moieties can include, but are not limited to, cyclopentyl, cyclopentenyl, cyclohexyl, cyclohexenyl, and the like. For instance, bridging atom $E^1$, $R^1$, and $R^2$ can form a cyclopentyl or cyclohexyl moiety. Heteroatom-substituted cyclic groups can be formed with nitrogen, oxygen, or sulfur heteroatoms, for example, when $E^1$ is C. While these heterocyclic groups can have up to 12 or 18 carbons atoms, the heterocyclic groups can be 3-membered, 4-membered, 5-membered, 6-membered, or 7-membered groups in some aspects of this invention.

In one aspect of the present invention, $R^1$ and $R^2$ are independently H or a hydrocarbyl group having up to 12 carbon atoms. Accordingly, $R^1$ and $R^2$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In another aspect, $R^1$ and $R^2$ independently can be a hydrocarbyl group having up to 12 carbon atoms; alternatively, up to 10 carbon atoms; or alternatively, up to 8 carbon atoms. In some aspects, $R^1$ and $R^2$ independently can be an alkyl or alkenyl group having up to 12 carbon atoms, while in other aspects, $R^1$ and $R^2$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl, and the like.

In another aspect, $R^1$ and $R^2$ are the same, and both are methyl, or ethyl, or propyl, or butyl, or pentyl, or phenyl. In another aspect, $R^1$ and $R^2$ are independently H or an alkyl or a terminal alkenyl group having up to 8 carbon atoms. In yet another aspect, at least one of $R^1$ and $R^2$ is a terminal alkenyl group having up to 8 carbon atoms or, alternatively, up to 6 carbon atoms.

$R^3$ in the above formulas is H or a hydrocarbyl or hydrocarbylsilyl group having up to 18 carbon atoms. In one aspect, $R^3$ can be hydrocarbyl group having up to 12 carbon atoms, while in another aspect, $R^3$ can be a hydrocarbylsilyl group having up to 12 carbon atoms (e.g., $R^3$ can be trimethylsilyl). In another aspect, $R^3$ can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In yet another aspect, $R^3$ is an alkyl or an alkenyl group (e.g., a terminal alkenyl group) having up to 12 carbon atoms; alternatively, up to 8 carbon atoms; or alternatively, up to 6 carbon atoms. In still another aspect, $R^3$ is methyl, ethyl, propyl, butyl, pentyl, or hexyl.

It is contemplated in aspects of the invention that, in formula (I), $M^1$ can be Zr or Hf, $X^1$ and $X^2$ can be Cl, and $E^1$ can be C or Si. Additionally, or alternatively, $R^1$, $R^2$, and $R^3$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In a further aspect, $R^1$, $R^2$, and $R^3$ independently can be methyl, ethyl, propyl, butyl, pentyl, hexyl, heptyl, or octyl.

Non-limiting examples of ansa-metallocene compounds having formula (I) that can be produced using the methods described herein include, but are not limited to, the following:

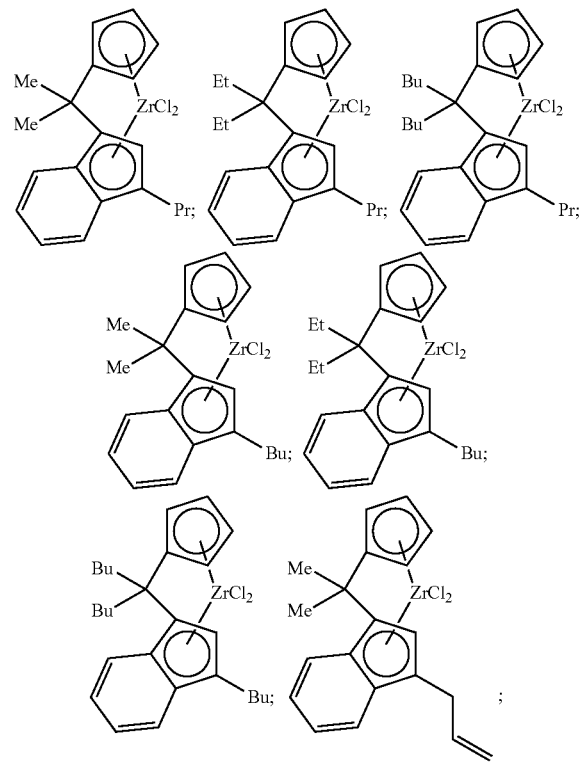

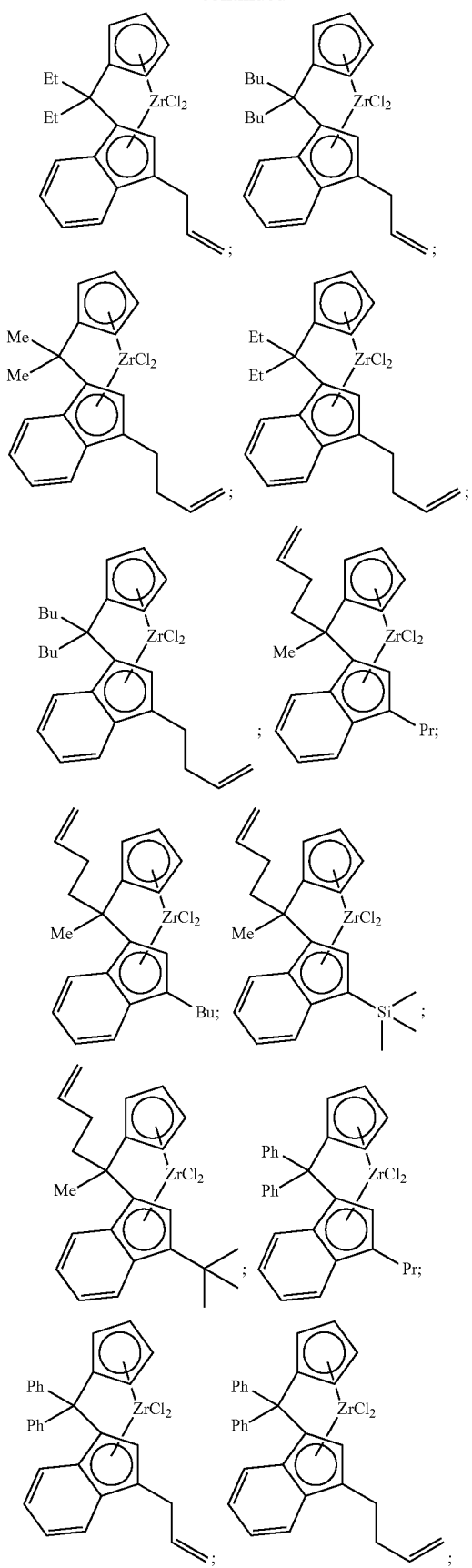
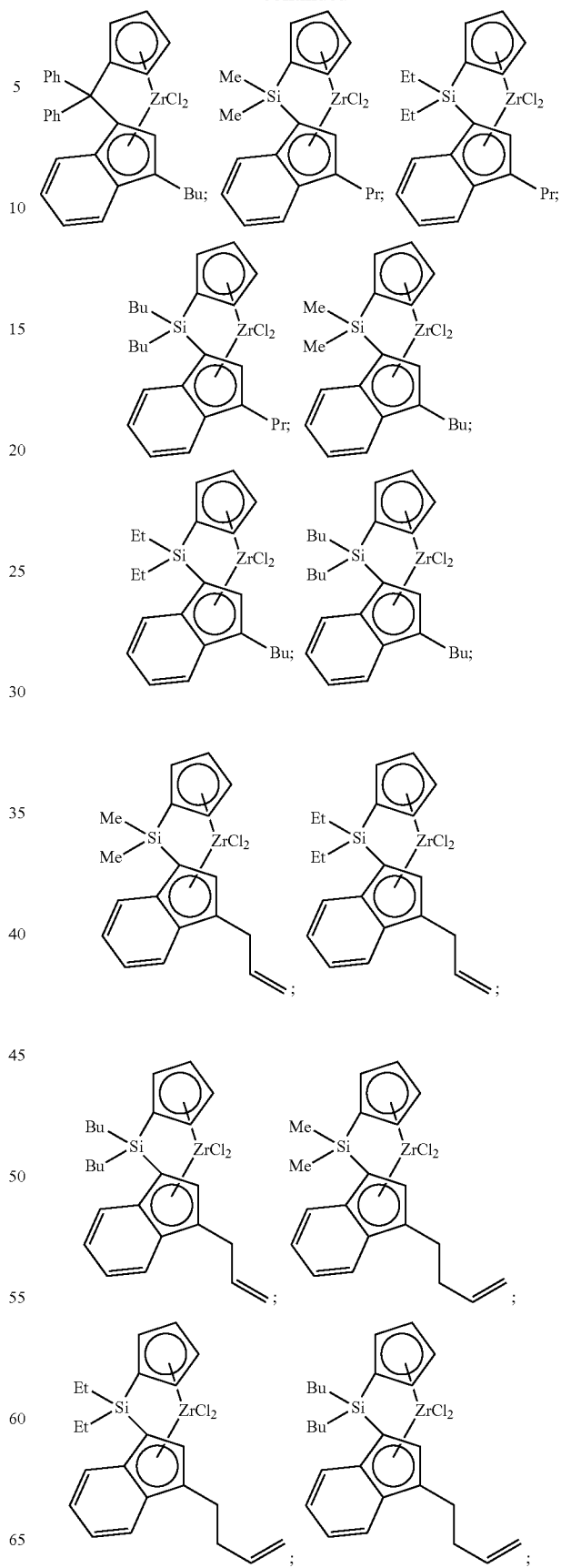

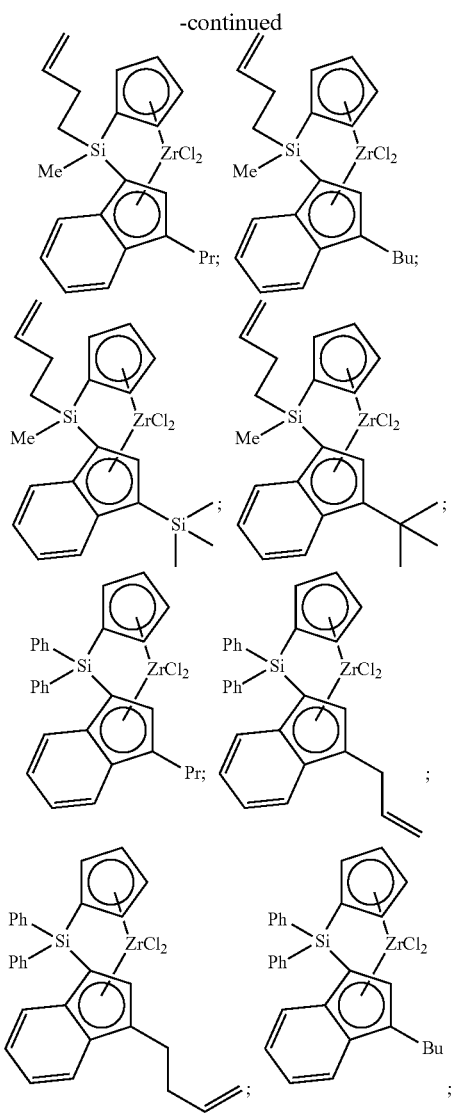

and the like, or any combination thereof.

In accordance with aspects of the method of making a metallocene compound having formula (I), the first strong base and the second strong base independently can comprise a lithium, sodium, or potassium atom, or a combination thereof. For example, the first strong base and the second strong base independently can comprise an alkyl lithium, an alkyl sodium, an alkyl potassium, lithium hydride, sodium hydride, potassium hydride, or any combination thereof. Illustrative and non-limiting examples of suitable materials that can be employed as the first strong base and/or the second strong base can include MeLi, n-BuLi, t-BuLi, n-hexylLi, LiCH$_2$SiMe$_3$, LiCH$_2$Ph, LiCH$_2$CMe$_3$, LiH, NaH, KH, or any combination of these materials. Applicants contemplate that the first strong base and/or the second strong base can comprise one or more than one of these compounds. Further, the first strong base and the second strong base can be the same compound.

The first solvent, the second solvent, the third solvent, and the fourth solvent utilized in the method of making a metallocene compound having formula (I) from a fulvene and a substituted indenyl independently can comprise an ether. As an example, the first solvent, the second solvent, the third solvent, and the fourth solvent independently can comprise a C$_4$ to C$_{20}$ ether; alternatively, a C$_4$ to C$_{10}$ ether; or alternatively, a C$_4$ to C$_8$ ether. In another aspect, the first solvent, the second solvent, the third solvent, and the fourth solvent independently can comprise diethyl ether, diisopropyl ether, di-n-propyl ether, di-n-butyl ether, diphenyl ether, methyl ethyl ether, methyl t-butyl ether, dihydrofuran, tetrahydrofuran (THF), 1,2-dimethoxyethane, and the like, or any combination of more than one of these materials. In a further aspect, the first solvent, the second solvent, the third solvent, and the fourth solvent independently can comprise diethyl ether, THF, or combinations thereof. It is also contemplated that two or more of the first solvent, the second solvent, the third solvent, and the fourth solvent can be the same ether solvent.

The optional hydrocarbon co-solvent employed in step (iv) can comprise one or more aliphatic hydrocarbons, aromatic hydrocarbons, or combinations thereof. Aliphatic hydrocarbons which may be useful as a co-solvent include C$_5$ to C$_{20}$ hydrocarbons, or alternatively, C$_5$ to C$_{10}$ hydrocarbons, and may be cyclic or acyclic and include linear or branched isomers, unless otherwise specified. Non-limiting examples of suitable acyclic aliphatic solvents include pentane, hexane, heptane, octane, and the like, and combinations thereof. Non-limiting examples of suitable cyclic aliphatic solvents include cyclopentane, cyclohexane, methyl cyclopentane, methyl cyclohexane, and the like, and combinations thereof. Aromatic hydrocarbons which may be useful as a solvent include C$_6$ to C$_{20}$ aromatic hydrocarbons; or alternatively, C$_6$ to C$_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. In one aspect, the optional hydrocarbon co-solvent employed can comprise pentane, hexane, heptane, octane, cyclopentane, cyclohexane, methyl cyclopentane, methyl cyclohexane, benzene, toluene, xylene, ethylbenzene, or combinations of two or more of these solvents. In a further aspect, the optional hydrocarbon co-solvent can comprise pentane, hexane, heptane, octane, cyclopentane, cyclohexane, methyl cyclopentane, methyl cyclohexane, or a combination thereof.

In accordance with aspects of this invention, the compound having formula (IVa), formula (IVb), or a combination thereof, is the limiting reactant in steps (i) and (ii). For instance, the molar ratio of the first strong base to the compound having formula (IVa), formula (IVb), or a combination thereof, can be within a range from about 2:1 to about 1:1. In another aspect, the molar ratio of the first strong base to the compound having formula (IVa), formula (IVb), or a combination thereof, in step (i) is in a range from about 1.8:1 to about 1:1, from about 1.6:1 to about 1:1, from about 1.4:1 to about 1:1, from about 1.2:1 to about 1:1, or from about 1.1:1 to about 1:1. Any molar ratios disclosed herein are meant to include the total moles of each respective component, for instance, to include circumstances where more than one first strong base is utilized and/or where more than one compound having formula (IVa) or formula (IVb) is employed and/or where a combination or mixture of isomers having formula (IVa) and formula (IVb) are employed. Thus, if a mixture of two bases was used, the total moles of both bases would be used in calculating a molar ratio. Likewise, if a mixture of isomers having formula (IVa) and formula (IVb) was used, the total moles of the mixture of isomers would be used in calculating a molar ratio.

In the synthesis method provided above, the molar ratio of the compound having formula (III) to the compound having formula (IVa), formula (IVb), or a combination thereof, generally falls within a range from about 2:1 to about 1:1; alternatively, from about 1.8:1 to about 1:1; alternatively, from about 1.6:1 to about 1:1; alternatively, from about 1.4:1 to about 1:1; or alternatively, from about 1.2:1 to about 1:1.

In steps (iii) and (iv) of a method of making a metallocene compound having formula (I), the compound having formula (Va), formula (Vb), or a combination thereof, can be the limiting reactant. Typical molar ratios of the second strong base to the compound having formula (Va), formula (Vb), or a combination thereof, in step (iii) can be in a range from about 3:1 to about 2:1. In some aspects, the molar ratio of the second strong base to the compound having formula (Va), formula (Vb), or a combination thereof, can be in a range from about 2.9:1 to about 2:1, from about 2.8:1 to about 2:1, from about 2.7:1 to about 2:1, from about 2.6:1 to about 2:1, from about 2.5:1 to about 2:1; from about 2.4:1 to about 2:1, or from about 2.2:1 to about 2:1.

The molar ratio of $M^1X^1X^2L^1L^2$ to the compound having formula (Va), formula (Vb), or a combination thereof, often can be within a range from about 1.8:1 to about 1:1. For instance, the molar ratio can be in a range from about 1.6:1 to about 1:1; alternatively, from about 1.5:1 to about 1:1; alternatively, from about 1.4:1 to about 1:1; alternatively, from about 1.3:1 to about 1:1; alternatively, from about 1.2:1 to about 1:1; or alternatively, from about 1.1:1 to about 1:1.

In accordance with this invention, when a limiting reactant is used in a step of any method disclosed herein, it is meant to infer that substantially all (i.e., at least 85%) of the limiting reactant reacts or is consumed in that step of the method. In some aspects, at least 88%, at least 90%, at least 92%, at least 95%, or at least 98% of the limiting reactant is consumed.

Independently, steps (i), (ii), (iii), and (iv) of the method of making a metallocene compound having formula (I) can be conducted at a variety of temperatures. The temperature at which the respective contacting steps are initiated can be the same as, or different from, the temperature at which the respective contacting steps are allowed to proceed or run for their duration. As an illustrative example, in step (i), the compound having formula (IVa), formula (IVb), or a combination thereof, and the first strong base can be combined initially at temperature T1 and, after combining, the temperature can be increased to a temperature T2 for a remainder of the contacting or reacting step to form the first mixture. In an aspect of this invention, the compound having formula (IVa), formula (IVb), or a combination thereof, and the first strong base can be combined initially at temperature in a range from about −80° C. to about 25° C.; alternatively, from about −60° C. to about 20° C.; alternatively, from about −40° C. to about 15° C.; alternatively, from about −20° C. to about 10° C.; or alternatively, from about −15° C. to about 5° C. In these and other aspects, after the initial combining, the temperature can be changed to another temperature—for instance, to room temperature in the 20° C. to 25° C. range—for the remainder of the duration of step (i) to form the first mixture.

Similarly, the first mixture and the compound having formula (III) in step (ii), the crude ligand product and the second strong base in step (iii), and the intermediate mixture and $M^1X^1X^2L^1L^2$ in step (iv), independently, can be combined initially at temperature in a range from about −80° C. to about 25° C.; alternatively, from about −60° C. to about 20° C.; alternatively, from about −40° C. to about 15° C.; alternatively, from about −20° C. to about 10° C.; or alternatively, from about −15° C. to about 5° C. In each step, after initially combining, the temperature can be changed to another temperature for the duration of the respective contacting step, for example, to a temperature in a range from about 15° C. to about 45° C., from about 20° C. to about 35° C., or from about 20° C. to about 25° C.

The appropriate contact or reaction time for each step in the method of making the metallocene compound having formula (I) can depend greatly upon the temperature and the reactant concentrations that are selected, among other variables. The initial combining time can be rapid (e.g., less than 5 minutes, less than 1 minute, or less than 30 seconds), but often, the initial combining of components in a particular step may be performed slowly, for example, in a time period ranging from about 15 minutes to about 8 hours; alternatively, from about 30 minutes to about 6 hours; or alternatively, from about 1 hour to about 4 hours. In general, the total contact or reaction time for a particular step in the method is greater than about 2 minutes, but less than about 24 hours. Often, the total time is from about 5 minutes to about 24 hours, from about 30 minutes to about 20 hours, from about 1 hour to about 18 hours, from about 1 hour to about 15 hours, or from about 2 hours to about 12 hours.

Advantageously, in aspects of this invention, the method of synthesizing a bridged cyclopentadienyl-indenyl metallocene having formula (I) from a fulvene and a substituted indenyl does not comprise a fine purification step. In this disclosure, a fine purification step can comprise distillation, chromatography, crystallization, or a combination of more than one of distillation, chromatography, and crystallization. Applicants contemplate that, by not employing distillation, chromatography, and/or crystallization, the metallocene synthesis can be performed in less time, with less complexity, and more cost effectively. Hence, the bridged cyclopentadienyl-indenyl metallocene can be synthesized from a fulvene and a substituted indenyl without using a fine purification step, such as distillation, chromatography, or crystallization, to increase the purity of any intermediate formed during the process. Additionally, no fine purification of the final reaction mixture containing the targeted bridged cyclopentadienyl-indenyl metallocene having formula (I) is required, although optionally, the metallocene compound having formula (I) can be purified, if desired, before use in a catalyst system or other end-use application.

Notwithstanding that methods of making bridged cyclopentadienyl-indenyl metallocenes disclosed herein may, in certain aspects, not include one or more of a distillation process, a chromatography process, and/or a crystallization process, other purification and/or isolation processes can be employed. Suitable purification and/or isolation processes that can be employed in this invention can include, but are not limited to, extraction, evaporation, washing, decanting, filtering, drying, and the like, or combinations thereof. For instance, a solvent and/or other volatile components of an intermediate or final reaction mixture can be removed via evaporation, for example, under reduced pressure.

In one aspect of this invention, the method of making a bridged cyclopentadienyl-indenyl metallocene having formula (I) from a fulvene and a substituted indenyl further comprises a step of removing the first strong base (e.g., any excess base), the first solvent, and/or the second solvent from the crude ligand product comprising the compound having formula (Va), formula (Vb), or a combination thereof. In this aspect, some or all of the first strong base, the first solvent, and/or the second solvent may be removed from the crude ligand product. The removal process can comprise one or more of extraction, evaporation, washing, decanting, filtering, drying, etc.

In another aspect, this invention contemplates a method further comprising a step of isolating the metallocene compound having formula (I) from the reaction mixture. The step of isolating can comprise one or more processes selected from extraction, evaporation, washing, decanting, filtering, drying, and the like, including combinations thereof. It is also contemplated that, if desired, a fine purification (e.g., crystallization or recrystallization) can be conducted on the final reaction mixture to further isolate and/or purify the metallocene compound having formula (I).

Synthesis of a Bridged Cyclopentadienyl-Indenyl Metallocene from Cyclopentadiene and a Substituted Indenyl In accordance with another aspect of the present invention, a method of making a metallocene compound having formula (I) is provided and, in this aspect, the method includes a fulvene synthesis from cyclopentadiene. This method comprises:

(1) contacting a compound having the formula:

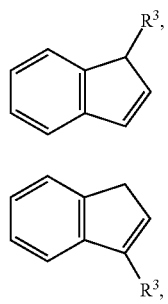

(IVa)

(IVb)

or a combination thereof, with a first strong base in the presence of a first solvent to form a first mixture;

(2) contacting cyclopentadiene with a compound having the formula:

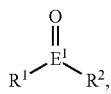

(II)

in the presence of a second solvent and pyrrolidine to form a crude fulvene product comprising a compound having the formula:

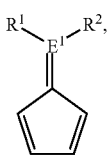

(III)

(3) contacting the first mixture with the crude fulvene product comprising the compound having formula (III) in the presence of a third solvent to form a crude ligand product comprising a compound having formula:

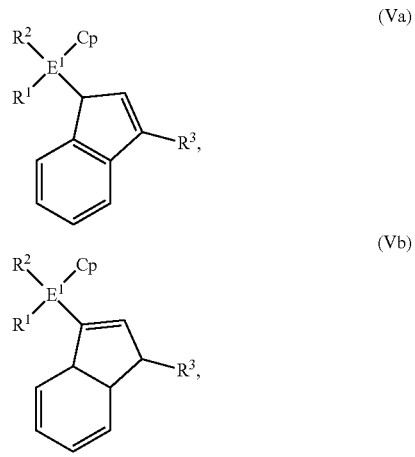

(Va)

(Vb)

or a combination thereof;

(4) contacting the crude ligand product comprising the compound having formula (Va), (Vb), or a combination thereof, with a second strong base in the presence of a fourth solvent to form an intermediate mixture comprising a dianion of the compound having formula (Va), (Vb), or a combination thereof; and (5) contacting the intermediate mixture comprising the dianion of the compound having formula (Va), (Vb), or a combination thereof, with $M^1X^1X^2L^1L^2$ in the presence of a fifth solvent and an optional hydrocarbon co-solvent to form a reaction mixture comprising the metallocene compound having formula (I);

wherein:

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C;

$R^1$ and $R^2$ are independently H, a hydrocarbyl group having up to 18 carbon atoms, or $R^1$ and $R^2$ are connected to a form a cyclic or heterocyclic group having up to 18 carbon atoms, wherein both $R^1$ and $R^2$ are not aryl groups; and $R^3$ is a hydrocarbyl or hydrocarbylsilyl group having up to 18 carbon atoms.

In this method, step (1) can be conducted before, after, or concurrently with step (2). That is, step (1) and step (2) can be performed in any order. As noted above, unless otherwise specified, formulas (I), (II), (III), (IVa), (IVb), (Va), and (Vb) above, any other structural formulas disclosed herein, and any species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

In this method of making a metallocene compound having formula (I), $M^1$, $X^1$, $X^2$, $L^1$, $L^2$, Cp, $E^1$, $R^1$, $R^2$, and $R^3$ can be any of the selections described above in relation to the method of synthesizing a bridged cyclopentadienyl-indenyl metallocene from a fulvene and a substituted indenyl. An exception to this generalization is that both $R^1$ and $R^2$, in a method of synthesizing a metallocene compound having formula (I) from cyclopentadiene and a substituted indenyl, are not aryl groups. For example, $R^1$ and $R^2$ independently can be H, a hydrocarbyl group having up to 18 carbon atoms, or $R^1$ and $R^2$ can be connected to a form a cyclic or heterocyclic group having up to 18 carbon atoms; however, both $R^1$ and $R^2$ are not phenyl groups.

It is contemplated in aspects of the invention that, in a method of synthesizing a bridged cyclopentadienyl-indenyl metallocene having formula (I) from cyclopentadiene and a substituted indenyl, $E^1$ is C. Further, $M^1$ can be Zr or Hf, and $X^1$ and $X^2$ can be Cl, in some aspects disclosed herein. In these and other aspects, $R^1$, $R^2$, and $R^3$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, or decenyl. For example, $R^1$, $R^2$, and $R^3$ independently can be methyl, ethyl, propyl, butyl, pentyl, hexyl, heptyl, or octyl.

The first strong base and the second strong base, as well as the first solvent, the second solvent, the third solvent, the fourth solvent, and the fifth solvent can be any of the base selections and solvent selections, respectively, described above in relation to the method of synthesizing a bridged cyclopentadienyl-indenyl metallocene from a fulvene and a substituted indenyl. Likewise, the optional hydrocarbon co-solvent employed in step (5) can comprise one or more of the aliphatic or aromatic co-solvents provided above, e.g., pentane, hexane, heptane, octane, cyclopentane cyclohexane, methyl cyclopentane, or combinations thereof. Additionally, the second solvent in step (2) can comprise an alcohol, such as, for example, a $C_1$ to $C_{20}$ alcohol; alternatively, a $C_1$ to $C_{10}$ alcohol; or alternatively, a $C_1$ to $C_6$ alcohol. In another aspect, the second solvent can comprise methanol, ethanol, propanol, butanol, pentanol, hexanol, and the like, or any combination of more than one of these materials.

In accordance with one aspect of this invention, the compound having formula (IVa), formula (IVb), or a combination thereof, can be the limiting reactant in steps (1) and (3), and the compound having formula (Va), formula (Vb), or a combination thereof, can be the limiting reactant in steps (4) and (5). The molar ratios provided above in the method of synthesizing a bridged cyclopentadienyl-indenyl metallocene from a fulvene and a substituted indenyl—i.e., the molar ratio of the first strong base to the compound having formula (IVa), formula (IVb), or a combination thereof; the molar ratio of the compound having formula (III) to the compound having formula (IVa), formula (IVb), or a combination thereof; the molar ratio of the second strong base to the compound having formula (Va), formula (Vb), or a combination thereof; and the molar ratio of $M^1X^1X^2L^1L^2$ to the compound having formula (Va), formula (Vb), or a combination thereof—also apply to this method of synthesizing a bridged cyclopentadienyl-indenyl metallocene from cyclopentadiene and a substituted indenyl.

In accordance with another aspect of this invention, the compound having formula (II) can be the limiting reactant in step (2). Suitable molar ratios of cyclopentadiene to the compound having formula (II) can be in the range from about 2:1 to about 1:1, such as, for instance, from about 1.8:1 to about 1:1, from about 1.6:1 to about 1:1, from about 1.4:1 to about 1:1, from about 1.2:1 to about 1:1, or from about 1.1:1 to about 1:1.

The molar ratio of pyrrolidine to the compound having formula (II) often can be within a range from about 2:1 to about 1:1. For instance, the molar ratio can be in a range from about 1.9:1 to about 1:1; alternatively, from about 1.8:1 to about 1:1; alternatively, from about 1.7:1 to about 1:1; alternatively, from about 1.6:1 to about 1:1; alternatively, from about 1.5:1 to about 1:1; alternatively, from about 1.4:1 to about 1:1; or alternatively, from about 1.3:1 to about 1:1.

As with steps (i), (ii), (iii), and (iv) above in the method of synthesizing a bridged cyclopentadienyl-indenyl metallocene from a fulvene and a substituted indenyl, steps (1), (2), (3), (4), and (5) in this method of synthesizing a bridged cyclopentadienyl-indenyl metallocene from cyclopentadiene and a substituted indenyl can be conducted, independently, over the same variety of temperatures and times. For instance, cyclopentadiene and the compound having formula (II) in step (2) can be combined initially at a temperature in a range from about −80° C. to about 25° C.; alternatively, from about −60° C. to about 20° C.; alternatively, from about −40° C. to about 15° C.; alternatively, from about −20° C. to about 10° C.; or alternatively, from about −15° C. to about 5° C. Additionally, after the initial combining, the temperature can be changed to another temperature (e.g., to a temperature in a range from about 15° C. to about 45° C., from about 20° C. to about 35° C., or from about 20° C. to about 25° C.) for the remainder of the duration of step (2) in order to form the crude fulvene product.

Furthermore, in aspects of this invention, the method of synthesizing a bridged cyclopentadienyl-indenyl metallocene having formula (I) from cyclopentadiene and a substituted indenyl does not comprise a fine purification step, i.e., distillation, chromatography, and/or crystallization. Suitable purification and/or isolation processes that can be employed in this method can include, but are not limited to, extraction, evaporation, washing, decanting, filtering, drying, and the like, or combinations thereof. Accordingly, in an aspect of this invention, the method of making a bridged cyclopentadienyl-indenyl metallocene having formula (I) from cyclopentadiene and a substituted indenyl further comprises a step of removing some or all of any unreacted cyclopentadiene, of the second solvent, and of pyrrolidine from the crude fulvene product comprising the compound having formula (III). One or more of extraction, evaporation, washing, decanting, filtering, drying, and the like, or combinations thereof, may be employed.

Synthesis of a Bridged Cyclopentadienyl-Indenyl Metallocene from a Fulvene and Indene In accordance with another aspect of the present invention, a method of making a metallocene compound having formula (I) is provided and, in this aspect, the method includes a substituted indenyl synthesis from indene. This method comprises:

(a) contacting indene with a first strong base in the presence of a first solvent to form a de-protonated indenyl mixture;

(b) contacting the de-protonated indenyl mixture with $R^3$-L to form a second mixture comprising a compound having the formula:

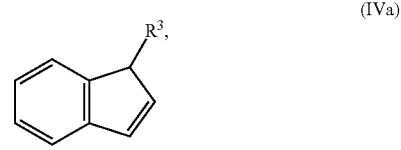

(IVa)

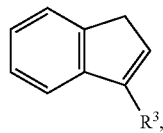

or a combination thereof;

(c) contacting the second mixture comprising the compound having formula (IVa), (IVb), or a combination thereof, with a second strong base in the presence of a second solvent to form a third mixture;

(d) contacting the third mixture with a compound having the formula:

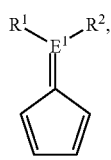

in the presence of a third solvent to form a crude ligand product comprising a compound having the formula:

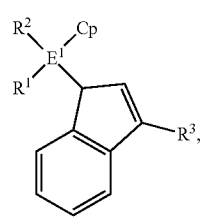

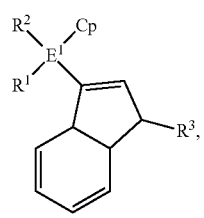

or a combination thereof;

(e) contacting the crude ligand product comprising the compound having formula (Va), (Vb), or a combination thereof, with a third strong base in the presence of a fourth solvent to form an intermediate mixture comprising a dianion of the compound having formula (Va), (Vb), or a combination thereof; and (f) contacting the intermediate mixture comprising the dianion of the compound having formula (Va), (Vb), or a combination thereof, with $M^1X^1X^2L^1L^2$ in the presence of a fifth solvent and an optional hydrocarbon co-solvent to form a reaction mixture comprising the metallocene compound having formula (I);

wherein:

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C, Si, Ge, or Sn;

$R^1$ and $R^2$ are independently H, a hydrocarbyl group having up to 18 carbon atoms, or $R^1$ and $R^2$ are connected to a form a cyclic or heterocyclic group having up to 18 carbon atoms;

$R^3$ is a hydrocarbyl or hydrocarbylsilyl group having up to 18 carbon atoms; and L is F; Cl; Br; I; $SO_3CF_3$; or $SO_3R$, wherein R is an alkyl, aryl, or alkylaryl group having up to 18 carbon atoms.

In this method of making a metallocene compound having formula (I), $M^1$, $X^1$, $X^2$, $L^1$, $L^2$, Cp, $E^1$, $R^1$, $R^2$, and $R^3$ can be any of the selections described above in relation to the method of synthesizing a bridged cyclopentadienyl-indenyl metallocene from a fulvene and a substituted indenyl.

As noted above, L can be F; Cl; Br; I; $SO_3CF_3$; or $SO_3R$, wherein R is an alkyl, aryl, or alkylaryl group having up to 18 carbon atoms or, alternatively, up to 12 carbon atoms. In one aspect, L can be F, Cl, Br, I, or $SO_3CF_3$. In another aspect, L can be F, Cl, Br, or I. Yet, in another aspect, L can be F; alternatively, L can be Cl; alternatively, L can be Br; or alternatively, L can be I.

It is contemplated in aspects of the invention that, in a method of synthesizing a bridged cyclopentadienyl-indenyl metallocene having formula (I) from a fulvene and indene, $M^1$ can be Zr or Hf, $X^1$ and $X^2$ can be Cl, $E^1$ can be C or Si, and L can be Cl or Br. In these and other aspects, $R^1$, $R^2$, and $R^3$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In a further aspect, $R^1$, $R^2$, and $R^3$ independently can be methyl, ethyl, propyl, butyl, pentyl, hexyl, heptyl, or octyl.

The first strong base, the second strong base, and the third strong base, as well as the first solvent, the second solvent, the third solvent, the fourth solvent, and the fifth solvent can be any of the base selections and solvent selections, respectively, described above in relation to the method of synthesizing a bridged cyclopentadienyl-indenyl metallocene from a fulvene and a substituted indenyl. Likewise, the optional hydrocarbon co-solvent employed in step (f) can comprise one or more of the aliphatic or aromatic co-solvents provided above.

In accordance with one aspect of this invention, the compound having formula (IVa), formula (IVb), or a combination thereof, can be the limiting reactant in steps (c) and (d), and the compound having formula (Va), formula (Vb), or a combination thereof, can be the limiting reactant in steps (e) and (f). The molar ratios provided above in the method of synthesizing a bridged cyclopentadienyl-indenyl metallocene from a fulvene and a substituted indenyl—i.e., the molar ratio of the compound having formula (III) to the compound having formula (IVa), formula (IVb), or a combination thereof; and the molar ratio of $M^1X^1X^2L^1L^2$ to the compound having formula (Va), formula (Vb), or a combination thereof—also apply to this method of synthesizing a bridged cyclopentadienyl-indenyl metallocene from a fulvene and indene.

In accordance with another aspect of this invention, the molar ratio of the second strong base to the compound having formula (IVa), formula (IVb), or a combination thereof, in step (c) is in a range from about 2:1 to about 1:1, from about 1.8:1 to about 1:1, from about 1.6:1 to about 1:1, from about 1.4:1 to about 1:1, from about 1.2:1 to about 1:1, or from about 1.1:1 to about 1:1. In step (e), the molar ratio of the third strong base to the compound having formula (Va), formula (Vb), or a combination thereof, can be in a range from about 3:1 to about 2:1, from about 2.9:1 to about 2:1, from about 2.8:1 to about 2:1, from about 2.7:1 to about 2:1, from about 2.6:1 to about 2:1, from about 2.5:1 to about 2:1; from about 2.4:1 to about 2:1, or from about 2.2:1 to about 2:1.

In accordance with yet another aspect of this invention, the first strong base can be the limiting reactant in steps (a) and (b). Suitable molar ratios of indene to the first strong base can be in the range from about 2:1 to about 1:1, such as, for instance, from about 1.8:1 to about 1:1, from about 1.6:1 to about 1:1, from about 1.4:1 to about 1:1, from about 1.2:1 to about 1:1, or from about 1.1:1 to about 1:1. Applicants contemplate that minimizing the formation of a di-substituted indenyl may be beneficial in the subsequent ligand and/or metallocene synthesis steps.

The molar ratio of $R^3$-L to the first strong base often can be within a range from about 2:1 to about 1:1. For instance, the molar ratio can be in a range from about 1.8:1 to about 1:1; alternatively, from about 1.6:1 to about 1:1; alternatively, from about 1.5:1 to about 1:1; alternatively, from about 1.4:1 to about 1:1; alternatively, from about 1.3:1 to about 1:1; alternatively, from about 1.2:1 to about 1:1; or alternatively, from about 1.1:1 to about 1:1.

As with steps (i), (ii), (iii), and (iv) above in the method of synthesizing a bridged cyclopentadienyl-indenyl metallocene from a fulvene and a substituted indenyl, steps (a), (b), (c), (d), (e), and (f) in this method of synthesizing a bridged cyclopentadienyl-indenyl metallocene from a fulvene and indene can be conducted, independently, over the same variety of temperatures and times. For instance, indene and the first strong base in step (a) and/or the de-protonated indenyl mixture and $R^3$-L in step (b), independently, can be combined initially at a temperature in a range from about −80° C. to about 25° C.; alternatively, from about −60° C. to about 20° C.; alternatively, from about −40° C. to about 15° C.; alternatively, from about −20° C. to about 10° C.; or alternatively, from about −15° C. to about 5° C. Additionally, after the initial combining, the respective temperature can be changed to another temperature (e.g., to a temperature in a range from about 15° C. to about 45° C., from about 20° C. to about 35° C., or from about 20° C. to about 25° C.) for the remainder of the duration of step (a) to form the de-protonated indenyl mixture and/or for the remainder of the duration of step (b) to form the second mixture.

Additionally, in aspects of this invention, the method of synthesizing a bridged cyclopentadienyl-indenyl metallocene having formula (I) from a fulvene and indene does not comprise a fine purification step, i.e., distillation, chromatography, and/or crystallization. Suitable purification and/or isolation processes that can be employed in this method can include, but are not limited to, extraction, evaporation, washing, decanting, filtering, drying, and the like, or combinations thereof. Accordingly, in an aspect of this invention, the method of making a bridged cyclopentadienyl-indenyl metallocene having formula (I) from a fulvene and indene further comprises a step of removing some or all of any unreacted indene and/or $R^3$-L from the second mixture. One or more of extraction, evaporation, washing, decanting, filtering, drying, and the like, or combinations thereof, may be employed.

Synthesis of a Bridged Cyclopentadienyl-Indenyl Metallocene from Cyclopentadiene and Indene In accordance with another aspect of the present invention, a method of making a metallocene compound having formula (I) is provided and, in this aspect, the method includes both a fulvene synthesis from cyclopentadiene and a substituted indenyl synthesis from indene. This method comprises:

(A) contacting indene with a first strong base in the presence of a first solvent to form a de-protonated indenyl mixture;

(B) contacting the de-protonated indenyl mixture with $R^3$-L to form a second mixture comprising a compound having the formula:

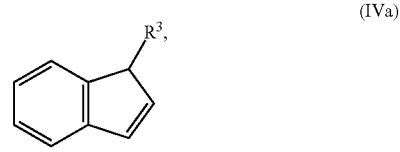

(IVa)

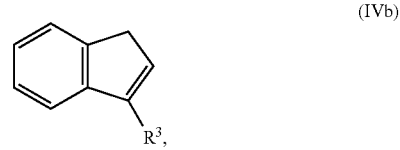

(IVb)

or a combination thereof;

(C) contacting cyclopentadiene with a compound having the formula:

(II)

in the presence of a second solvent and pyrrolidine to form a crude fulvene product comprising a compound having the formula:

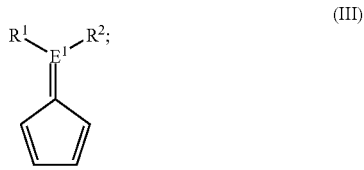

(III)

(D) contacting the second mixture comprising the compound having formula (IVa), (IVb), or a combination thereof, with a second strong base in the presence of a third solvent to form a deprotonated Ind-$R^3$ mixture;

(E) contacting the deprotonated Ind-$R^3$ mixture with the crude fulvene product comprising the compound having formula (III) in the presence of a fourth solvent to form a crude ligand product comprising a compound having the formula:

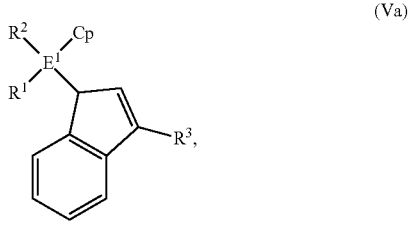

(Va)

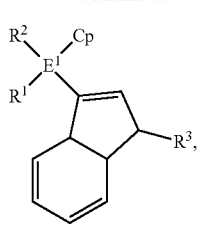

(Vb)

or a combination thereof;

(F) contacting the crude ligand product comprising the compound having formula (Va), (Vb), or a combination thereof, with a third strong base in the presence of a fifth solvent to form an intermediate mixture comprising a dianion of the compound having formula (Va), (Vb), or a combination thereof; and (G) contacting the intermediate mixture comprising the dianion of the compound having formula (Va), (Vb), or a combination thereof, with $M^1X^1X^2L^1L^2$ in the presence of a sixth solvent and an optional hydrocarbon co-solvent to form a reaction mixture comprising the metallocene compound having formula (I);

wherein:

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C;

$R^1$ and $R^2$ are independently H, a hydrocarbyl group having up to 18 carbon atoms, or $R^1$ and $R^2$ are connected to a form a cyclic or heterocyclic group having up to 18 carbon atoms, wherein both $R^1$ and $R^2$ are not aryl groups;

$R^3$ is a hydrocarbyl or hydrocarbylsilyl group having up to 18 carbon atoms; and L is F; Cl; Br; I; $SO_3CF_3$; or $SO_3R$, wherein R is an alkyl, aryl, or alkylaryl group having up to 18 carbon atoms.

In this method, step (C) can be performed at any time prior to step (E). That is, step (C) can be conducted before, after, or concurrently with any of steps (A), (B), and/or (D).

In this method of making a metallocene compound having formula (I), $M^1$, $X^1$, $X^2$, $L^1$, $L^2$, Cp, $E^1$, $R^1$, $R^2$, and $R^3$ can be any of the selections described above in relation to the method of synthesizing a bridged cyclopentadienyl-indenyl metallocene from a fulvene and a substituted indenyl. An exception to this generalization is that both $R^1$ and $R^2$, in a method of synthesizing a metallocene compound having formula (I) from cyclopentadiene and indene, are not aryl groups. For example, $R^1$ and $R^2$ independently can be H, a hydrocarbyl group having up to 18 carbon atoms, or $R^1$ and $R^2$ can be connected to a form a cyclic or heterocyclic group having up to 18 carbon atoms; however, both $R^1$ and $R^2$ are not phenyl groups.

As noted above, L can be F; Cl; Br; I; $SO_3CF_3$; or $SO_3R$, wherein R is an alkyl, aryl, or alkylaryl group having up to 18 carbon atoms or, alternatively, up to 12 carbon atoms. In one aspect, L can be F, Cl, Br, I, or $SO_3CF_3$. In another aspect, L can be F, Cl, Br, or I. Yet, in another aspect, L can be F; alternatively, L can be Cl; alternatively, L can be Br; or alternatively, L can be I.

It is contemplated in aspects of the invention that, in a method of synthesizing a bridged cyclopentadienyl-indenyl metallocene having formula (I) from cyclopentadiene and indene, $E^1$ is C. Further, $M^1$ can be Zr or Hf, $X^1$ and $X^2$ can be Cl, and L can be Cl or Br, in some aspects disclosed herein. In these and other aspects, $R^1$, $R^2$, and $R^3$ independently can be methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, or decenyl. And further, $R^1$, $R^2$, and $R^3$ independently can be methyl, ethyl, propyl, butyl, pentyl, hexyl, heptyl, or octyl, in some aspects of this invention.

A generic reaction scheme for synthesizing a bridged cyclopentadienyl-indenyl metallocene having formula (I) from starting materials cyclopentadiene and indene is illustrated below:

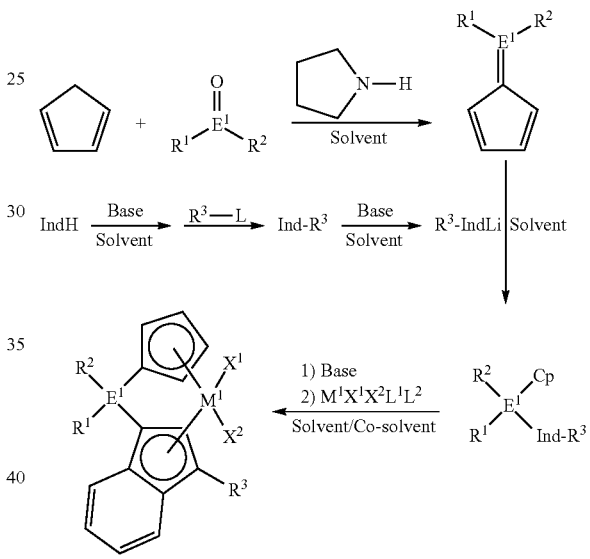

The first strong base, the second strong base, and the third strong base, as well as the first solvent, the second solvent, the third solvent, the fourth solvent, the fifth solvent, and the sixth solvent can be any of the base selections and solvent selections, respectively, described above in relation to the method of synthesizing a bridged cyclopentadienyl-indenyl metallocene from a fulvene and a substituted indenyl. Likewise, the optional hydrocarbon co-solvent employed in step (G) can comprise one or more of the aliphatic or aromatic co-solvents provided above, e.g., pentane, hexane, heptane, octane, cyclopentane, cyclohexane, methyl cyclopentane, or combinations thereof. Additionally, the second solvent in step (C) can comprise an alcohol, such as, for example, a $C_1$ to $C_{20}$ alcohol; alternatively, a $C_1$ to $C_{10}$ alcohol; or alternatively, a $C_1$ to $C_6$ alcohol. In another aspect, the second solvent can comprise methanol, ethanol, propanol, butanol, pentanol, hexanol, and the like, or any combination of more than one of these materials.

In accordance with aspects of this invention, the first strong base can be the limiting reactant in steps (A) and (B). Additionally, or alternatively, the compound having formula (II) can be the limiting reactant in step (C). Additionally, or alternatively, the compound having formula (IVa), formula (IVb), or a combination thereof, can be the limiting reactant in steps (D) and (E). Additionally, or alternatively, the compound having formula (Va), formula (Vb), or a combination thereof, can be the limiting reactant in steps (F) and (G).

The molar ratios provided above in the method of synthesizing a bridged cyclopentadienyl-indenyl metallocene from a fulvene and a substituted indenyl—i.e., the molar ratio of the compound having formula (III) to the compound having formula (IVa), formula (IVb), or a combination thereof; and the molar ratio of $M^1X^1X^2L^1L^2$ to the compound having formula (Va), formula (Vb), or a combination thereof—also apply to this method of synthesizing a bridged cyclopentadienyl-indenyl metallocene from cyclopentadiene and indene.

Suitable molar ratios of indene to the first strong base in step (A) can be in the range from about 2:1 to about 1:1, such as, for instance, from about 1.8:1 to about 1:1, from about 1.6:1 to about 1:1, from about 1.4:1 to about 1:1, from about 1.2:1 to about 1:1, or from about 1.1:1 to about 1:1.

The molar ratio of $R^3$-L to the first strong base often can be within a range from about 2:1 to about 1:1. For instance, the molar ratio can be in a range from about 1.8:1 to about 1:1; alternatively, from about 1.6:1 to about 1:1; alternatively, from about 1.5:1 to about 1:1; alternatively, from about 1.4:1 to about 1:1; alternatively, from about 1.3:1 to about 1:1; alternatively, from about 1.2:1 to about 1:1; or alternatively, from about 1.1:1 to about 1:1.

Suitable molar ratios of cyclopentadiene to the compound having formula (II) in step (C) can be in the range from about 2:1 to about 1:1. Molar ratios in a range from about 1.8:1 to about 1:1, from about 1.6:1 to about 1:1, from about 1.4:1 to about 1:1, from about 1.2:1 to about 1:1, or from about 1.1:1 to about 1:1, can be employed in an aspect of this invention. The molar ratio of pyrrolidine to the compound having formula (II) often can be within a range from about 2:1 to about 1:1. For instance, the molar ratio can be in a range from about 1.9:1 to about 1:1; alternatively, from about 1.8:1 to about 1:1; alternatively, from about 1.7:1 to about 1:1; alternatively, from about 1.6:1 to about 1:1; alternatively, from about 1.5:1 to about 1:1; alternatively, from about 1.4:1 to about 1:1; or alternatively, from about 1.3:1 to about 1:1.

In accordance with another aspect of this invention, the molar ratio of the second strong base to the compound having formula (IVa), formula (IVb), or a combination thereof, in step (D) is in a range from about 2:1 to about 1:1, from about 1.8:1 to about 1:1, from about 1.6:1 to about 1:1, from about 1.4:1 to about 1:1, from about 1.2:1 to about 1:1, or from about 1.1:1 to about 1:1.

In step (F), the molar ratio of the third strong base to the compound having formula (Va), formula (Vb), or a combination thereof, can be in a range from about 3:1 to about 2:1, from about 2.9:1 to about 2:1, from about 2.8:1 to about 2:1, from about 2.7:1 to about 2:1, from about 2.6:1 to about 2:1, from about 2.5:1 to about 2:1, from about 2.4:1 to about 2:1, or from about 2.2:1 to about 2:1.

As with steps (i), (ii), (iii), and (iv) above in the method of synthesizing a bridged cyclopentadienyl-indenyl metallocene from a fulvene and a substituted indenyl, steps (A), (B), (C), (D), (E), (F), and (G) in this method of synthesizing a bridged cyclopentadienyl-indenyl metallocene from cyclopentadiene and indene can be conducted, independently, over the same variety of temperatures and times. For instance, indene and the first strong base in step (A) and/or the de-protonated indenyl mixture and $R^3$-L in step (B), independently, can be combined initially at a temperature in a range from about −80° C. to about 25° C.; alternatively, from about −60° C. to about 20° C.; alternatively, from about −40° C. to about 15° C.; alternatively, from about −20° C. to about 10° C.; or alternatively, from about −15° C. to about 5° C.

Additionally, after the initial combining, the respective temperature can be changed to another temperature (e.g., to a temperature in a range from about 15° C. to about 45° C., from about 20° C. to about 35° C., or from about 20° C. to about 25° C.) for the remainder of the duration of step (A) to form the de-protonated indenyl mixture and/or for the remainder of the duration of step (B) to form the second mixture.

Additionally, in aspects of this invention, the method of synthesizing a bridged cyclopentadienyl-indenyl metallocene having formula (I) from cyclopentadiene and indene does not comprise a fine purification step, i.e., distillation, chromatography, and/or crystallization. Suitable purification and/or isolation processes that can be employed in this method can include, but are not limited to, extraction, evaporation, washing, decanting, filtering, drying, and the like, or combinations thereof.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Nuclear Magnetic Resonance (NMR) spectra were obtained on a Varian Mercury Plus 300 NMR spectrometer operating at 300 MHz for $^1$H NMR (CDCl$_3$ solvent, referenced against the peak of residual CHCl$_3$ at 7.24 ppm) and 75 MHz for $^{13}$C NMR (CDCl$_3$ solvent, referenced against central line of CHCl$_3$ at 77.00 ppm).

Molecular weights and molecular weight distributions were obtained using a PL 220 SEC high temperature chromatography unit (Polymer Laboratories) with trichlorobenzene (TCB) as the solvent, with a flow rate of 1 mL/minute at a temperature of 145° C. BHT (2,6-di-tert-butyl-4-methylphenol) at a concentration of 0.5 g/L was used as a stabilizer in the TCB. An injection volume of 200 μL was used with a nominal polymer concentration of 1.5 mg/mL. Dissolution of the sample in stabilized TCB was carried out by heating at 150° C. for 5 hours with occasional, gentle agitation. The columns used were three PLgel Mixed A LS columns (7.8× 300 mm) and were calibrated with a broad linear polyethylene standard (Phillips Marlex® BHB 5003) for which the molecular weight had been determined.

The fluorided silica-coated alumina activator-support (abbreviated AS) employed in Examples 3-4 was prepared in accordance with the following procedure. Silica-coated alumina grade Siral 28M, obtained from Sasol Co., was heated at a rate of 100° C./hr up to 600° C. in fluidizing air (0.1 ft/sec), and then held at 600° C. for 3 hours. After discharging to a glass mixing vessel, the silica-coated alumina was impregnated with 3 mL/g of a solution of ammonium bifluoride in methanol. This solution contained about 0.033 g of dissolved NH$_4$HF$_2$ per mL of methanol. The incipient-wetted powder was then dried in a vacuum oven at 60° C. for 18 hours. Then, 10 g of this material was calcined in fluidizing air (0.1 ft/sec) at 600° C. for 3 hours. After this calcining step, the fluidized bed was flushed with dry nitrogen for 30 minutes at 100° C., and the fluorided silica-coated alumina activator-support (AS) was transferred into an air-tight container under dry nitrogen until later use.

Example 1

Synthesis of a Bridged Cyclopentadienyl-Indenyl Metallocene

A bridged cyclopentadienyl-indenyl metallocene compound with the following structure was synthesized in Example 1 (abbreviated MET I):

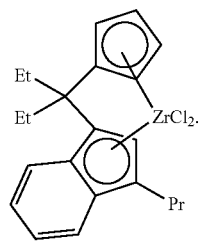

The general reaction scheme provided below was employed:

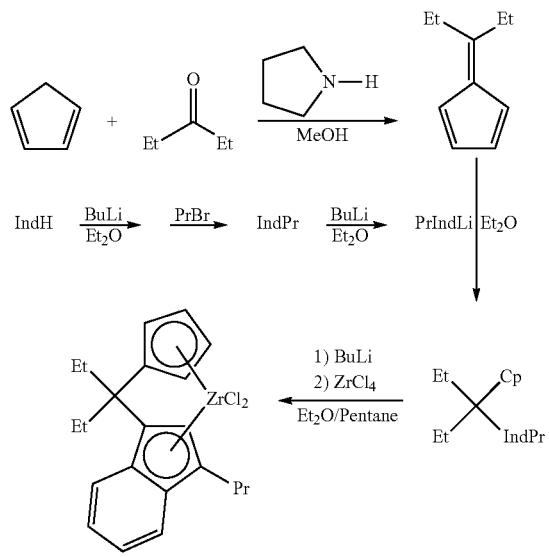

The fulvene compound was synthesized by generally following the procedure described in Stone and Little, Journal of Organic Chemistry, 1984, 49 (11) 1849-1853, the disclosure of which is incorporated herein by reference in its entirety. Starting with 3-pentanone (86 g, 1 mol) dissolved in methanol (500 mL) and cooled down in an ice-water bath, cyclopentadiene (85.8 g, 1.3 mol) was added, followed by the addition of pyrrolidine (106.5 g, 1.5 mol). The addition rate of pyrrolidine was controlled by maintaining the temperature of the reaction solution below 10° C. The mixture was stirred for 1 hr at about 5 to 10° C. Then, the mixture was warmed up to room temperature (~23° C.) and stirred overnight at room temperature (overnight is approximately 12 hours); alternatively, about 2 hours may be an adequate reaction time). The reaction was quenched with acetic acid (86 mL of 17.4 M, 1.5 mol) in an ice-water bath. The addition rate of acetic acid was controlled by maintaining the temperature of the solution below 10° C. The mixture was stirred in an ice-bath for 15 min, then warmed up to room temperature and stirred for an additional 15 min. The mixture was extracted with pentane (800 mL). The aqueous layer was extracted with another 500 mL of pentane. The two pentane solutions were combined and washed with water (4×600 mL). The pentane solution was then dried over sodium sulfate anhydrate. Removal of the solvent gave the product as a yellow brown liquid (127 g, ~92% pure by GC).

Propylindene was synthesized using the following procedure. Starting with indene (72.9 mL of 90% pure, 0.56 mol) dissolved in diethyl ether (300 mL) and cooled down in an ice-water bath, nBuLi (50 mL of 10 M in hexanes, 0.5 mol) was added dropwise over 1 hr. The mixture was allowed to slowly warm to room temperature over 3 hours and then stirred overnight at room temperature. The resultant indenyl-lithium solution was added dropwise to 1-bromopropane (69.4 mL, 0.764 mol) dissolved in diethyl ether (100 mL) and cooled down in an ice-water bath. The resultant solution was allowed to slowly warm to room temperature over 3 hours, stirred overnight at room temperature, and then quenched with water (500 mL). Diethyl ether (500 mL) was added and the organic layer was separated. The organic layer was washed with 2% HCl aqueous solution (500 mL) and water (2×250 mL). The solution was dried over magnesium sulfate anhydrate and the volatiles were evacuated. The unreacted indene and bromopropane were removed at 50° C. under vacuum (0.8 mmHg). The product was obtained as a pale yellow liquid (75.3 g, ~98% pure by GC).

The ligand was synthesized using the following procedure. Starting with propylindene (79 g of 98% pure by GC, 0.49 mol) dissolved in diethyl ether (500 mL) and cooled down in an ice-water bath, nBuLi (50 mL of 10 M in hexanes, 0.5 mol) was added dropwise. The mixture was allowed to slowly warm to room temperature over 3 hours and then stirred overnight at room temperature. A large amount of precipitate was formed. Diethyl ether (500 mL) was added to dissolve the precipitate. The mixture was cooled down in an ice-water bath, followed by the addition of diethyl fulvene (89.3 g of 92% pure by GC, 0.61 mol). The resultant solution was allowed to slowly warm to room temperature over 3 hours, stirred overnight at room temperature, and then the mixture was quenched with water (500 mL) and the organic layer separated. The organic layer was washed with 2% HCl aqueous solution (500 mL) and water (2×250 mL). The solution was dried over magnesium sulfate anhydrate and the volatiles were evacuated. The final ligand product was obtained as a viscous liquid (160 g, 77% pure by GC).

The bridged cyclopentadienyl-indenyl metallocene was synthesized from the ligand using the following procedure. Starting with the crude ligand (30.1 g of 77% pure by GC, 79.4 mmol) dissolved in anhydrous $Et_2O$ (400 mL) and cooled down in an ice-water bath under nitrogen, n-BuLi (16 mL of 10 M in hexanes, 160 mmol) was added dropwise. The resultant mixture was slowly warmed to room temperature over 1 hr and then stirred overnight at room temperature. This mixture then was slowly added to $ZrCl_4$ (20.5 g, 88 mmol) suspended in a mixture of pentane (100 mL) and $Et_2O$ (100 mL) at 5 to 10° C. The resultant mixture was warmed to room temperature, stirred overnight, and then the solvent was partially removed under vacuum to reduce the total volume of the mixture to about 125 mL. The solid was separated by centrifuge and washed with pentane (2×200 mL). The washed solid was then extracted with $CH_2Cl_2$ (250 mL). Removal of the solvent from the CH$_2$Cl$_2$ extract gave the desired product MET I as an orange-yellow solid (27.1 g, 75.5% yield based on the ligand).

A sample of this final product containing MET I was dissolved in D-chloroform to form a solution for analysis by $^1$H-NMR. $^1$H-NMR confirmed the presence of the desired metallocene compound, MET I, as illustrated in FIG. 1.

Example 2

Synthesis of a Bridged Cyclopentadienyl-Indenyl Metallocene Using a Purified Ligand Example 2 employed substantially the same procedure as Example 1, with the exception that the ligand product was purified prior to the synthesis of the bridged cyclopentadienyl-indenyl metallocene MET I from the ligand.

The ligand product was purified by column chromatography using the following procedure. The crude ligand was dissolved in a minimum amount of heptane and was then loaded into a column packed with 170-400 mesh silica gel, available from Fisher Scientific. The mixture was eluted with heptane. The purified ligand was obtained by evaporating the remaining solvent.

Figure 2:
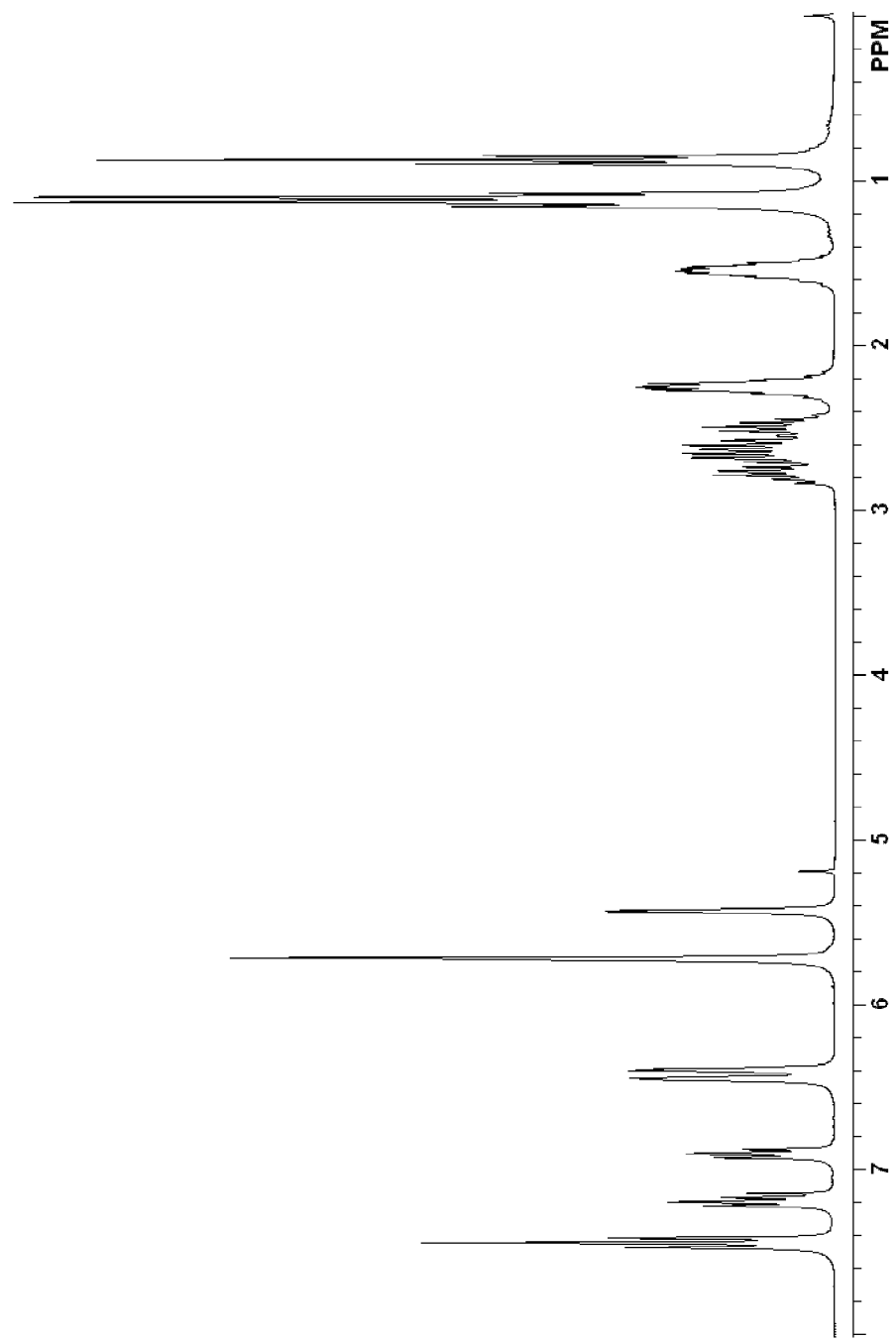
FIG. 2 presents a $^1$H-NMR plot of the final product of Example 2 containing MET I.

FIG. 2 illustrates a $^1$H-NMR plot of the final product of Example 2, containing MET I, made from the purified ligand.

Examples 3-4

Polymers Produced Using MET I Synthesized in Examples 1-2

Example 3 utilized MET I produced in accordance with Example 1, while Example 4 utilized MET I produced in accordance with Example 2, using a purified ligand.

The respective MET I metallocene was dissolved in 1-octene (20 mL, 14.3 g), followed by the addition of triisobutylaluminum (TIBA, 1 mL of 1M solution) at room temperature. The mixture was stirred at room temperature for about 2 minutes. Approximately 250 mg of the activator-support (AS) were then added. The resultant mixture was stirred for 4 hours at room temperature before the reaction was quenched with 0.5 mL of water. The viscous reaction product was diluted with pentane, and the liquid phase was separated from the solid. The solvent was removed at about 60-70° C. under vacuum to obtain a clear, colorless viscous product.

Figure 3:
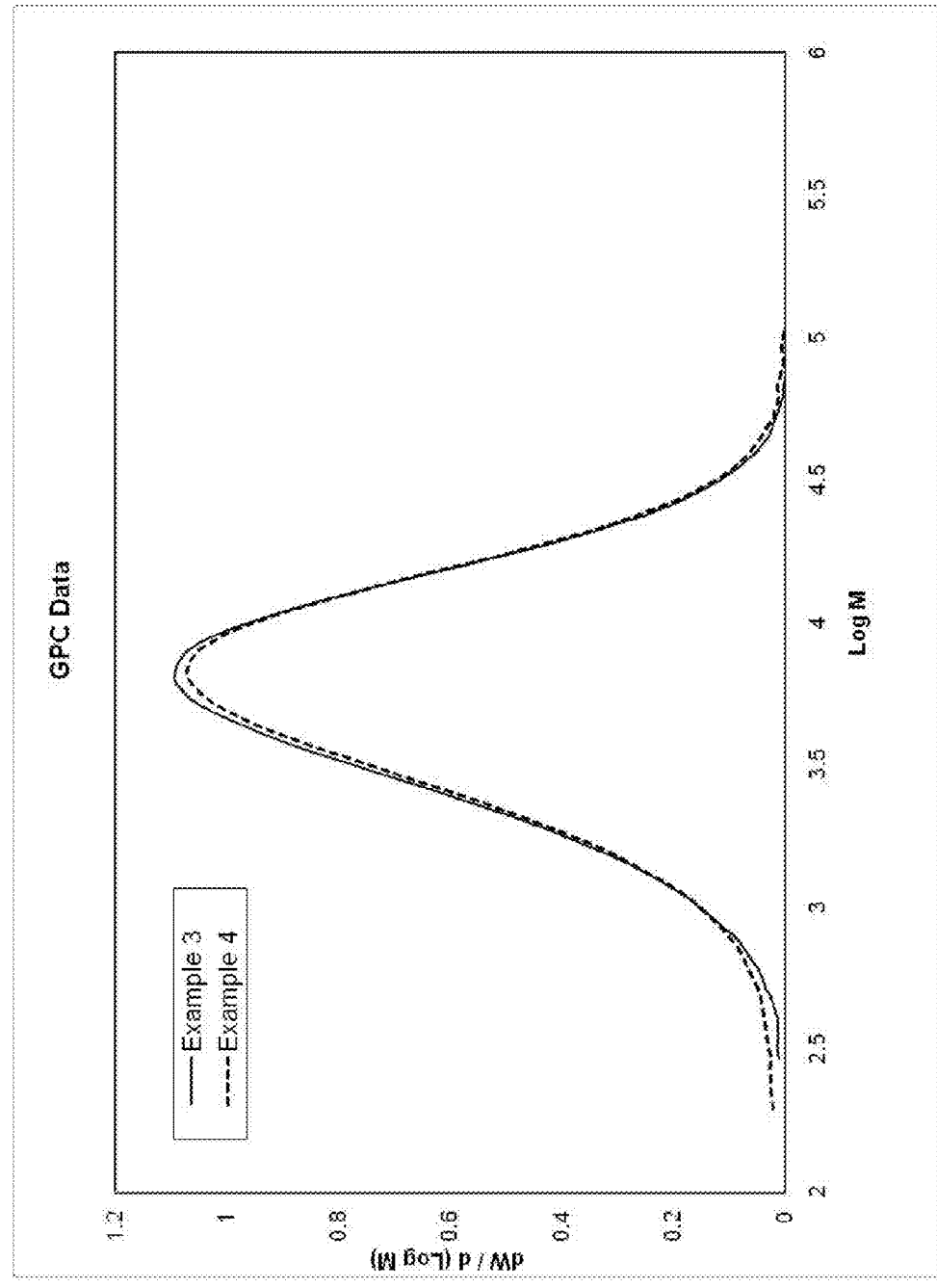
FIG. 3 presents a plot of the molecular weight distributions of the polymers of Examples 3-4.

The polymerization conditions for Examples 3-4 are summarized in Table I, while FIG. 3 illustrates the molecular weight distributions of the polymers of Examples 3-4. As shown in Table I and FIG. 3, any impurities present accompanying MET I produced in Example 1 did not negatively impact the catalyst activity or the polymer properties of Example 3. The amount of polyoctene produced in Example 3 was essentially the same as that of Example 4. Additionally, FIG. 3 demonstrates that the polymers of Examples 3 and 4 have virtually identical molecular weight distributions.

We claim:

1. A method of making a metallocene compound having the formula:

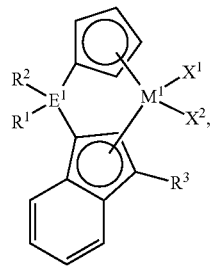

(I)

the method comprising:

(i) contacting a first compound having the formula:

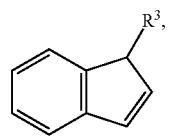

(IVa)

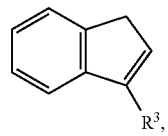

(IVb)

or a combination thereof, with a first strong base in the presence of a first solvent to form a first mixture;

(ii) contacting the first mixture with a second compound having the formula:

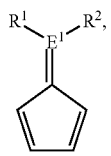

(III)

TABLE I

Polymerization Conditions for Examples 3-4.

| Example | MET I (mg) | Time (hr) | 1-octene (g) | Activator-Support | Alkyl Aluminum | Polyoctene Produced (g) | Product Description |
|---|---|---|---|---|---|---|---|
| 3 | 3 | 4 | 14.3 | 250 mg AS | 198 mg TIBA | 9.4 | Colorless viscous liquid |
| 4 | 3 | 4 | 14.3 | 250 mg AS | 198 mg TIBA | 9.5 | Colorless viscous liquid | in the presence of a second solvent to form a crude ligand product comprising a third compound having the formula:

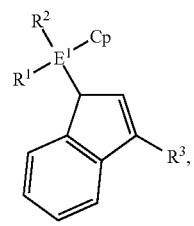
(Va)

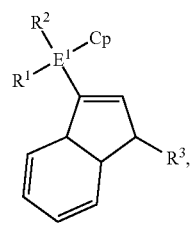
(Vb)

or a combination thereof;
(iii) contacting the crude ligand product with a second strong base in the presence of a third solvent to form an intermediate mixture comprising a dianion of the third compound; and
(iv) contacting the intermediate mixture with $M^1X^1X^2L^1L^2$ in the presence of a fourth solvent and an optional hydrocarbon co-solvent to form a reaction mixture comprising the metallocene compound having formula (I);

wherein:
the method does not comprise a fine purification step comprising distillation, chromatography, crystallization, or a combination thereof;
$M^1$ is Ti, Zr, or Hf;
$X^1$ and $X^2$ are independently F; Cl; Br; I; $SO_3CF_3$; or $SO_3R$, wherein R is an alkyl, aryl, or alkylaryl group having up to 18 carbon atoms;
$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;
Cp is a cyclopentadienyl group;
$E^1$ is C, Si, Ge, or Sn;
$R^1$ and $R^2$ are independently H, a hydrocarbyl group having up to 18 carbon atoms, or $R^1$ and $R^2$ are connected to a form a cyclic or heterocyclic group having up to 18 carbon atoms; and
$R^3$ is a hydrocarbyl or hydrocarbylsilyl group having up to 18 carbon atoms.

2. The method of claim 1, wherein:
$M^1$ is Zr or Hf;
$X^1$ and $X^2$ are independently F, Cl, Br, or I;
$E^1$ is C or Si; and
$R^1$, $R^2$, and $R^3$ are independently H or a hydrocarbyl group having up to 12 carbon atoms.

3. The method of claim 2, wherein:
$X^1$ and $X^2$ are Cl;
$E^1$ is C; and
$R^1$, $R^2$, and $R^3$ are independently methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl.

4. The method of claim 1, wherein the metallocene compound having formula (I) is:

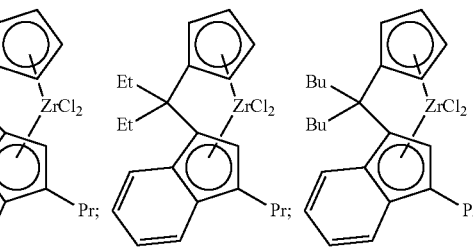

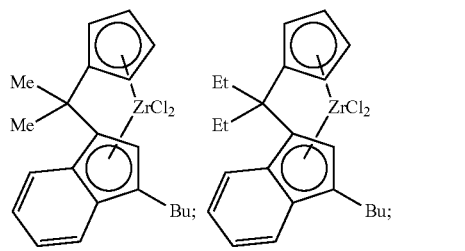

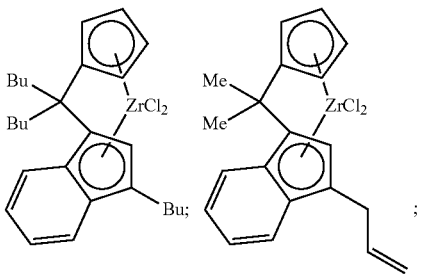

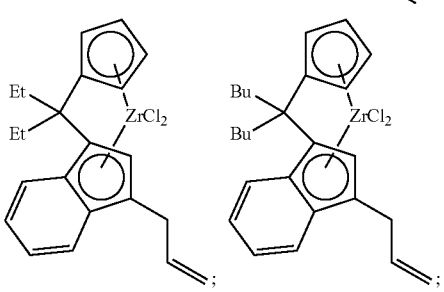

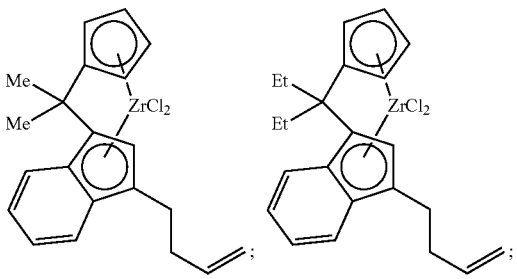

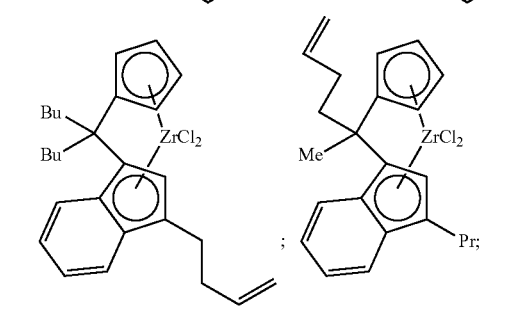

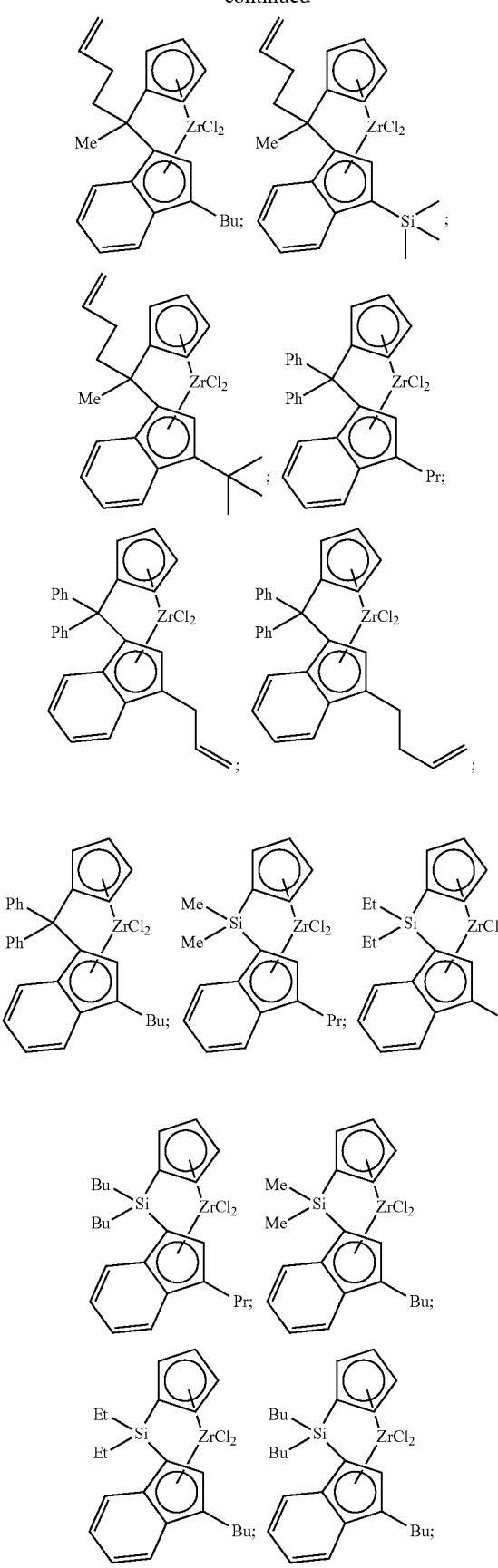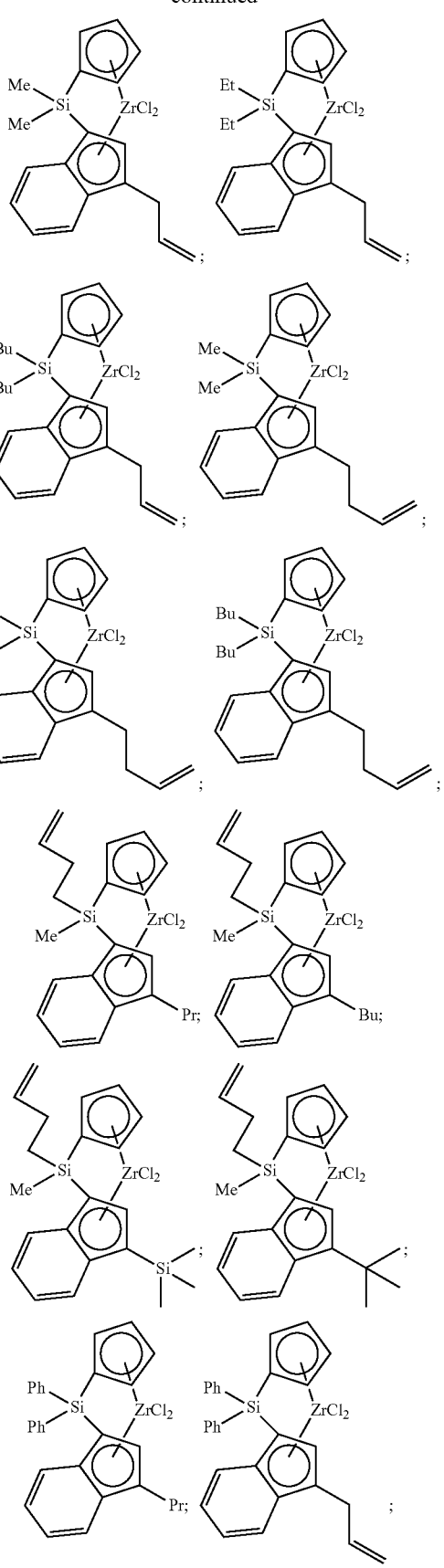

-continued

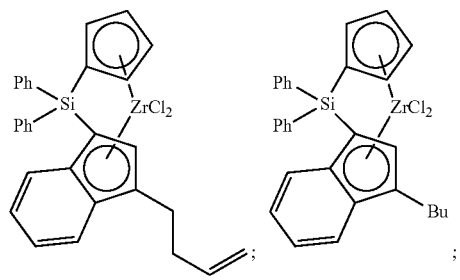

or any combination thereof.

5. The method of claim 1, wherein the first strong base and the second strong base independently comprise MeLi, n-BuLi, t-BuLi, n-hexylLi, LiCH$_2$SiMe$_3$, LiCH$_2$Ph, LiCH$_2$CMe$_3$, LiH, NaH, KH, or a combination thereof.

6. The method of claim 1, wherein the first solvent, the second solvent, the third solvent, and the fourth solvent independently comprise an ether.

7. The method of claim 1, wherein the optional hydrocarbon co-solvent comprises an aliphatic hydrocarbon, an aromatic hydrocarbon, or a combination thereof.

8. The method of claim 1, wherein the first compound is the limiting reactant in steps (i) and (ii).

9. The method of claim 1, wherein the third compound is the limiting reactant in steps (iii) and (iv).

10. The method of claim 1, wherein:
   a molar ratio of the first strong base to the first compound is in a range from about 2:1 to about 1:1;
   a molar ratio of the second compound to the first compound is in a range from about 2:1 to about 1:1;
   a molar ratio of the second strong base to the third compound is in a range from about 3:1 to about 2:1; or
   a molar ratio of M$^1$X$^1$X$^2$L$^1$L$^2$ to the third compound is in a range from about 1.5:1 to about 1:1; or
   any combination thereof.

11. The method of claim 1, further comprising a step of isolating the metallocene compound having formula (I) from the reaction mixture.

12. A method of making a metallocene compound having the formula:

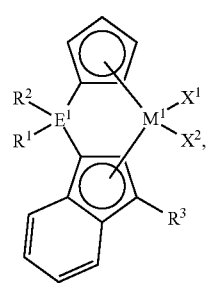 (I)

the method comprising:
   (1) contacting a first compound having the formula:

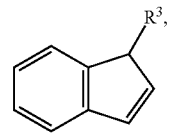 (IVa)

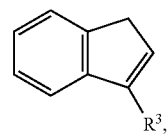 (IVb)

or a combination thereof,
with a first strong base in the presence of a first solvent to form a first mixture;
   (2) contacting cyclopentadiene with a second compound having the formula:

 (II)

in the presence of a second solvent and pyrrolidine to form a crude fulvene product comprising a third compound having the formula:

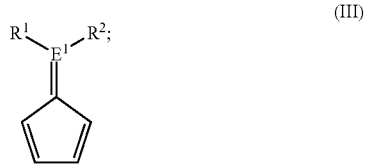 (III)

(3) contacting the first mixture with the crude fulvene product in the presence of a third solvent to form a crude ligand product comprising a fourth compound having formula:

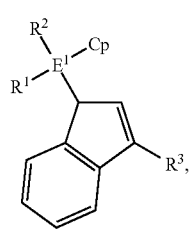 (Va)

(Vb)

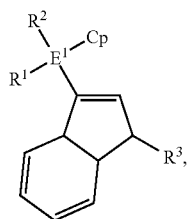

or a combination thereof;

(4) contacting the crude ligand product with a second strong base in the presence of a fourth solvent to form an intermediate mixture comprising a dianion of the fourth compound; and (5) contacting the intermediate mixture with $M^1X^1X^2L^1L^2$ in the presence of a fifth solvent and an optional hydrocarbon co-solvent to form a reaction mixture comprising the metallocene compound having formula (I);

wherein:

the method does not comprise a fine purification step comprising distillation, chromatography, crystallization, or a combination thereof;

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C;

$R^1$ and $R^2$ are independently H, a hydrocarbyl group having up to 18 carbon atoms, or $R^1$ and $R^2$ are connected to a form a cyclic or heterocyclic group having up to 18 carbon atoms, wherein both $R^1$ and $R^2$ are not aryl groups;

$R^3$ is a hydrocarbyl or hydrocarbylsilyl group having up to 18 carbon atoms; and step (1) can be conducted before, after, or concurrently with step (2).

13. The method of claim 12, wherein the second compound is the limiting reactant in step (2).

14. The method of claim 12, wherein:

a molar ratio of cyclopentadiene to the second compound is in a range from about 2:1 to about 1:1; or a molar ratio of pyrrolidine to the second compound is in a range from about 2:1 to about 1:1; or both.

15. A method of making a metallocene compound having the formula:

(I)

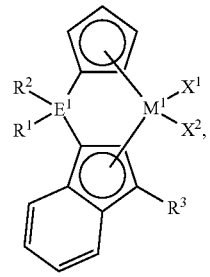

the method comprising:

(a) contacting indene with a first strong base in the presence of a first solvent to form a de-protonated indenyl mixture;

(b) contacting the de-protonated indenyl mixture with $R^3$-L to form a second mixture comprising a first compound having the formula:

(IVa)

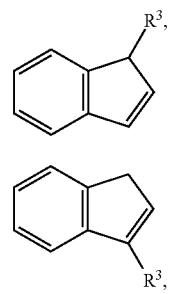

(IVb)

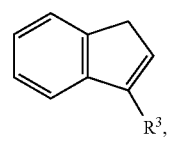

or a combination thereof;

(c) contacting the second mixture with a second strong base in the presence of a second solvent to form a third mixture;

(d) contacting the third mixture with a second compound having the formula:

(III)

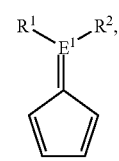

in the presence of a third solvent to form a crude ligand product comprising a third compound having the formula:

(Va)

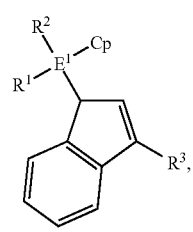

-continued

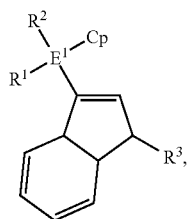
(Vb)

or a combination thereof;

(e) contacting the crude ligand product with a third strong base in the presence of a fourth solvent to form an intermediate mixture comprising a dianion of the third compound; and (f) contacting the intermediate mixture with $M^1X^1X^2L^1L^2$ in the presence of a fifth solvent and an optional hydrocarbon co-solvent to form a reaction mixture comprising the metallocene compound having formula (I);

wherein:

the first strong base is the limiting reactant in steps (a) and (b);

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C, Si, Ge, or Sn;

$R^1$ and $R^2$ are independently H, a hydrocarbyl group having up to 18 carbon atoms, or $R^1$ and $R^2$ are connected to a form a cyclic or heterocyclic group having up to 18 carbon atoms;

$R^3$ is a hydrocarbyl or hydrocarbylsilyl group having up to 18 carbon atoms; and L is F; Cl; Br; I; $SO_3CF_3$; or $SO_3R$, wherein R is an alkyl, aryl, or alkylaryl group having up to 18 carbon atoms.

16. The method of claim 15, wherein L is F, Cl, Br, or I.

17. The method of claim 15, wherein:
a molar ratio of indene to the first strong base is in a range from about 2:1 to about 1:1; or
a molar ratio of $R^3$-L to the first strong base is in a range from about 2:1 to about 1:1; or
both.

18. A method of making a metallocene compound having the formula:

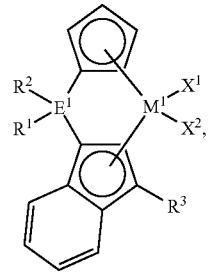
(I)

the method comprising:

(A) contacting indene with a first strong base in the presence of a first solvent to form a de-protonated indenyl mixture;

(B) contacting the de-protonated indenyl mixture with $R^3$-L to form a second mixture comprising a first compound having the formula:

(IVa)

(IVb)

or a combination thereof;

(C) contacting cyclopentadiene with a second compound having the formula:

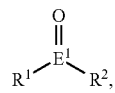
(II)

in the presence of a second solvent and pyrrolidine to form a crude fulvene product comprising a third compound having the formula:

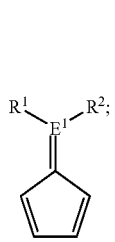
(III)

(D) contacting the second mixture with a second strong base in the presence of a third solvent to form a deprotonated Ind-$R^3$ mixture;

(E) contacting the deprotonated Ind-R³ mixture with the crude fulvene product in the presence of a fourth solvent to form a crude ligand product comprising a fourth compound having the formula:

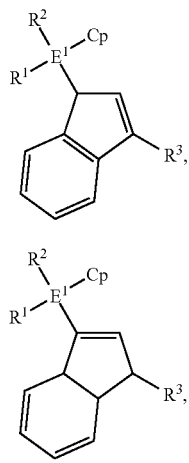

(Va)

(Vb)

or a combination thereof;

(F) contacting the crude ligand product with a third strong base in the presence of a fifth solvent to form an intermediate mixture comprising a dianion of the fourth compound; and (G) contacting the intermediate mixture with $M^1X^1X^2L^1L^2$ in the presence of a sixth solvent and an optional hydrocarbon co-solvent to form a reaction mixture comprising the metallocene compound having formula (I);

wherein:

the first strong base is the limiting reactant in steps (A) and (B);

$M^1$ is Ti, Zr, or Hf;

$X^1$ and $X^2$ are independently F; Cl; Br; I; $SO_3CF_3$; or $SO_3R$, wherein R is an alkyl, aryl, or alkylaryl group having up to 18 carbon atoms;

$L^1$ and $L^2$ are independently F; Cl; Br; I; methyl; benzyl; phenyl; H; $BH_4$; $SO_3CF_3$; $OBR_2$ or $SO_3R$, wherein R is an alkyl, aryl, or alkylaryl group having up to 18 carbon atoms; or a hydrocarbyloxide group, a hydrocarbylamino group, or a hydrocarbylsilyl group, any of which having up to 18 carbon atoms;

Cp is a cyclopentadienyl group;

$E^1$ is C;

$R^1$ and $R^2$ are independently H, a hydrocarbyl group having up to 18 carbon atoms, or $R^1$ and $R^2$ are connected to a form a cyclic or heterocyclic group having up to 18 carbon atoms, wherein both $R^1$ and $R^2$ are not aryl groups;

$R^3$ is a hydrocarbyl or hydrocarbylsilyl group having up to 18 carbon atoms;

L is F; Cl; Br; I; $SO_3CF_3$; or $SO_3R$, wherein R is an alkyl, aryl, or alkylaryl group having up to 18 carbon atoms; and step (C) can be performed at any time prior to step (E).

19. The method of claim 18, wherein:

a molar ratio of indene to the first strong base is in a range from about 1.8:1 to about 1:1; or a molar ratio of $R^3$-L to the first strong base is in a range from about 1.8:1 to about 1:1; or both.

20. The method of claim 15, wherein:

a molar ratio of indene to the first strong base is in a range from about 1.8:1 to about 1:1; or a molar ratio of $R^3$-L to the first strong base is in a range from about 1.8:1 to about 1:1; or both.

\* \* \* \* \*